(12) United States Patent
Tani et al.

(10) Patent No.: US 10,808,059 B2
(45) Date of Patent: Oct. 20, 2020

(54) POLYMER

(71) Applicant: CANON KABUSHIKI KAISHA, Tokyo (JP)

(72) Inventors: Yutaka Tani, Kawasaki (JP); Takeshi Sekiguchi, Kawasaki (JP); Keigo Mizusawa, Tokyo (JP); Ryuji Higashi, Kawasaki (JP); Masaru Sugita, Tokyo (JP); Isao Kawata, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 152 days.

(21) Appl. No.: 15/993,947

(22) Filed: May 31, 2018

(65) Prior Publication Data
US 2018/0355086 A1 Dec. 13, 2018

(30) Foreign Application Priority Data

Jun. 9, 2017 (JP) .................. 2017-114358

(51) Int. Cl.
*C08F 226/06* (2006.01)
*C08F 220/60* (2006.01)
(Continued)

(52) U.S. Cl.
CPC .......... *C08F 218/08* (2013.01); *C08F 212/08* (2013.01); *C08F 212/14* (2013.01);
(Continued)

(58) Field of Classification Search
CPC .. C08F 226/06; C08F 220/60; C08F 220/603; C08F 220/606
See application file for complete search history.

(56) References Cited

U.S. PATENT DOCUMENTS 2,881,155 A * 4/1959 Hankins .................. C08F 20/34
526/263
3,300,429 A * 1/1967 Glavis .................. C09D 125/00
524/516
(Continued)

FOREIGN PATENT DOCUMENTS

EP 629 672 * 6/1994 ........... C09D 157/00
JP 2010-59239 A * 3/2010 ........... C08F 220/36
WO WO 2011/107440 A1 * 9/2011 ........... C08F 220/06

OTHER PUBLICATIONS

Ying, H.; Zhang, Y.; Cheng, J. Nature Communications Feb. 4, 2014 p. 1-9. (Year: 2014).*

(Continued)

Primary Examiner — Rip A Lee
(74) Attorney, Agent, or Firm — Venable LLP

(57) ABSTRACT

To determine and detect 8-oxo-2'-deoxyguanosine in an aqueous sample solution with high sensitivity and specifically, provided is a polymer including a repetition structure represented by any one of the following general formulae 2 to 5, in which a group represented by any one of the following general formulae 6 to 11 is linked to the repetition structure represented by any one of the following general formulae 2 to 5 through a divalent linking group L.

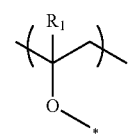

2

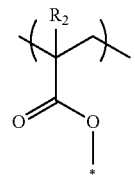

3

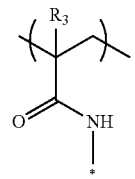

4

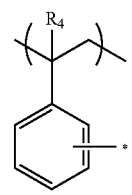

5

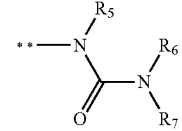

6

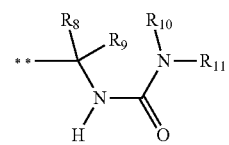

7

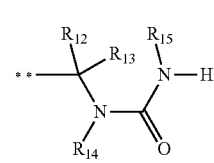

8

(Continued)

-continued

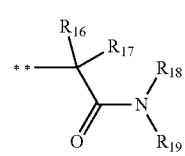

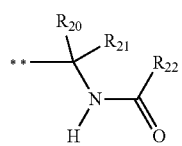

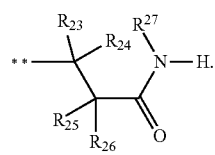

6 Claims, No Drawings

(51) Int. Cl.
| | |
|---|---|
| C08F 218/08 | (2006.01) |
| C08F 220/14 | (2006.01) |
| C08F 220/36 | (2006.01) |
| C08F 220/56 | (2006.01) |
| C08F 220/06 | (2006.01) |
| C08F 220/54 | (2006.01) |
| C08F 212/08 | (2006.01) |
| G01N 33/53 | (2006.01) |
| C08F 212/14 | (2006.01) |
| C08F 218/04 | (2006.01) |
| C08F 220/28 | (2006.01) |
| C08F 220/30 | (2006.01) |
| C08F 222/10 | (2006.01) |

(52) U.S. Cl.
CPC .......... *C08F 218/04* (2013.01); *C08F 220/06* (2013.01); *C08F 220/14* (2013.01); *C08F 220/36* (2013.01); *C08F 220/54* (2013.01); *C08F 220/56* (2013.01); *C08F 220/60* (2013.01); *G01N 33/5308* (2013.01); *C08F 220/281* (2020.02); *C08F 220/283* (2020.02); *C08F 220/301* (2020.02); *C08F 220/303* (2020.02); *C08F 220/365* (2020.02); *C08F 220/603* (2020.02); *C08F 220/606* (2020.02); *C08F 222/102* (2020.02); *G01N 2800/7009* (2013.01)

(56) References Cited

U.S. PATENT DOCUMENTS

| | | | | |
|---|---|---|---|---|
| 3,356,627 | A * | 12/1967 | Scott | C09D 125/00 |
| | | | | 524/516 |
| 4,436,887 | A * | 3/1984 | Chromecek | A61L 27/16 |
| | | | | 351/159.33 |
| 4,596,850 | A * | 6/1986 | Iovine | C08F 26/06 |
| | | | | 524/548 |
| 5,294,688 | A * | 3/1994 | Rehmer | C08F 224/00 |
| | | | | 522/152 |
| 9,365,745 | B2 * | 6/2016 | Gerst | C09J 133/14 |
| 2018/0305522 | A1 * | 10/2018 | Seki | C08K 5/357 |

OTHER PUBLICATIONS

Lingxin Chen et al., "Recent Advances in Molecular Imprinting Technology: Current Status, Challenges and Highlighted Applications," 40 Chem. Soc. Rev. 2922-2942 (Feb. 2011).

Ridvan Say et al., "Preparation of New Molecularly Imprinted Quartz Crystal Microbalance Flybride Sensor System for 8-Hydroxy-2'-Deoxyguanosine Determination," 640(1-2) Analytica Chimica Acta 82-86 (Mar. 2009).

Seki et al., U.S. Appl. No. 15/951,387, filed Apr. 12, 2018.

* cited by examiner

POLYMER

BACKGROUND OF THE INVENTION

Field of the Invention

The present invention relates to a polymer that can determine and detect 8-oxo-2'-deoxyguanosine (hereinafter described as "8OHdG") or a similar marker with high sensitivity and specifically.

Description of the Related Art

8OHdG has been attracting attention as an oxidative stress marker because 8OHdG directly reflects the amount of active oxygen produced in association with an environmental factor or metabolic activity in a living organism. Accurate measurement of the amount of 8OHdG present in a living organism or in urine is significant in researches on mutation, aging, and many diseases. In recent years, the selection, combination, and the like of a separation technology, a concentration technology, and an analysis approach have enabled the analysis of various compounds present in amounts at sub-ppt (one trillionth) levels. However, the analysis needs to pass through respective steps adapted to an object to be detected, such as optimum separation, optimum concentration, optimum qualitative analysis, and optimum quantitative analysis, in many cases.

The production amount of active oxygen is variable, and is hence desirably measured rapidly in various measurement environments. In addition, 8OHdG is liable to undergo a cross reaction with uric acid present in a large amount in a living organism, and hence an investigation needs to be made on a measurement method having high specific selectivity.

It has been known that the use of a resin having a molecular recognition function enables the amount of a chemical substance to be rapidly measured at relatively low cost under various environments (Chem. Soc. Rev., 2011, 40, p. 2922-2942, Non Patent Literature 1). Meanwhile, the method involves many problems in terms of specific selectivity. In addition, there is a report on the detection of the presence amount of 8OHdG with a QCM (Analytica Chimica Acta 640 (2009) p. 82-86, Non Patent Literature 2), and a molecular imprinting polymer has been used.

A problem to be solved by the present invention is to provide a method by which 8OHdG or a similar marker is detected simply, with high sensitivity, and specifically.

SUMMARY OF THE INVENTION

The inventors of the present invention have made extensive investigations for solving the problem, and as a result, have completed a polymer capable of adsorbing 8OHdG with high sensitivity and specifically. In addition, as a result of the foregoing, there can be provided a device that can determine and detect 8OHdG simply, with high sensitivity, and specifically.

Further features of the present invention will become apparent from the following description of exemplary embodiments.

DESCRIPTION OF THE EMBODIMENTS

Preferred embodiments of the present invention will now be described in detail in accordance with the accompanying drawings.

The present invention is described in detail below by way of a preferred embodiment.

<Polymer Represented by General Formula 1>

The inventors of the present invention have made investigations, and as a result, have found a polymer represented by the following general formula 1, which is capable of adsorbing 8OHdG with high sensitivity and specifically. In the polymer represented by the general formula 1, a group represented by B is bonded to a polymer main chain in which A is polymerized through a linking group L.

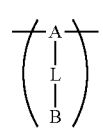

In the general formula 1,

is represented by any one of the following general formulae 2 to 5,

is represented by any one of the following general formulae 6 to 11, and

L represents a divalent linking group containing 1 to 3 carbon atoms for linking A and B:

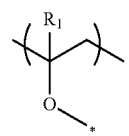

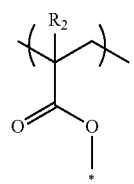

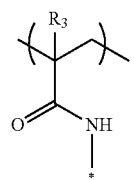

-continued

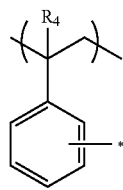

5

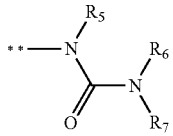

6

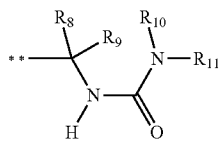

7

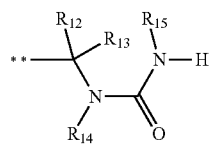

8

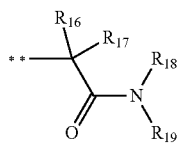

9

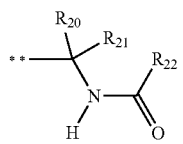

10

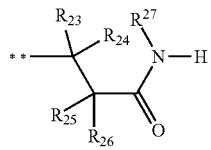

11 provided that in the general formulae 2 to 5, $R_1$ to $R_4$ each independently represent a hydrogen atom or a methyl group, and * represents a bonding position with L, and in the general formulae 6 to 11, $R_5$ to $R_{27}$ each independently represent any one of a hydrogen atom, a halogen atom, an alkyl group, an aryl group, a heteroaryl group, an aralkyl group, a hydroxy group, an amino group, a carboxyl group, a sulfo group, and a nitro group, $R_5$ and $R_6$, $R_6$ and $R_7$, $R_5$ and $R_9$, $R_9$ and $R_{10}$, $R_{10}$ and $R_{11}$, $R_{13}$ and $R_{15}$, $R_{17}$ and $R_{18}$, $R_{18}$ and $R_{19}$, $R_{21}$ and $R_{22}$, $R_{23}$ and $R_{24}$, and $R_{24}$ and $R_{27}$ may each independently be bonded to each other to form a cyclic structure, and ** represents a bonding position with L.

Further, in the general formula 1,

|
B may be represented by any one of the following general formulae 12 to 17:

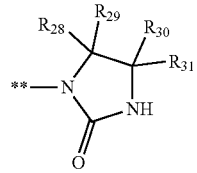

12

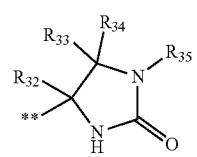

13

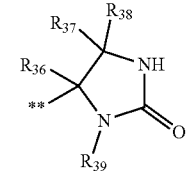

14

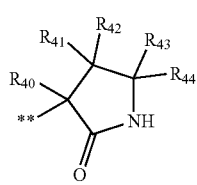

15

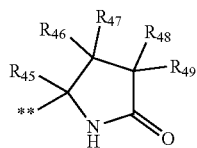

16

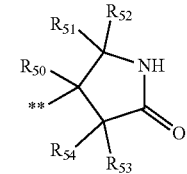

17 provided that in the general formulae 12 to 17, $R_{28}$ to $R_{54}$ each independently represent any one of a hydrogen atom, a halogen atom, an alkyl group, an aryl group, a heteroaryl group, an aralkyl group, a hydroxy group, an amino group, a carboxyl group, a sulfo group, and a nitro group, and ** represents a bonding position with L.

In addition, according to one embodiment of the present invention, there is provided a polymer including any one of repetition structures represented by the following general formulae 18 to 23:

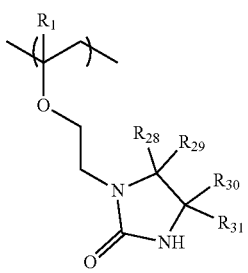

18

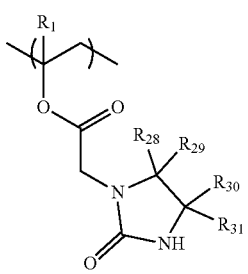

19

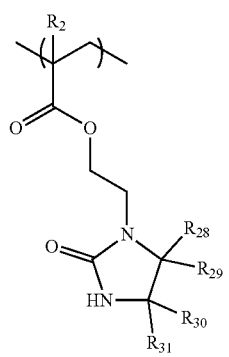

20

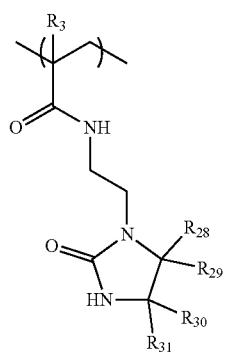

21

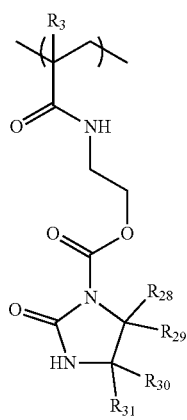

22

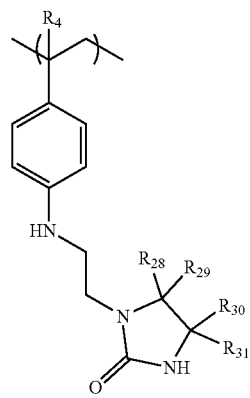

23 provided that in the general formulae 18 to 23, $R_1$ to $R_4$ each independently represent a hydrogen atom or a methyl group, and $R_{28}$ to $R_{31}$ each independently represent any one of a hydrogen atom, a halogen atom, an alkyl group, an aryl group, a heteroaryl group, an aralkyl group, a hydroxy group, an amino group, a carboxyl group, a sulfo group, and a nitro group.

<Molecular Recognition>

8OHdG is represented by the following structural formula C. 8OHdG has tautomers, and hence may also be represented by any one of structures represented by the following structural formulae C', C'', and C'''. Description is given below based typically on the structure represented by the structural formula C.

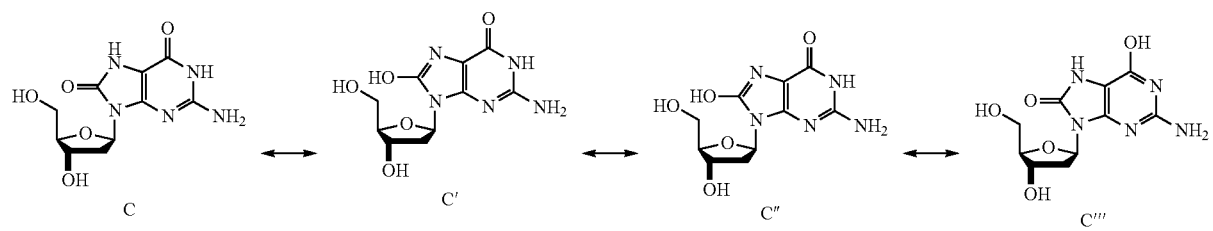

The mechanism via which the polymer in the embodiment of the present invention recognizes a molecule of 8OHdG with high sensitivity and specifically is assumed to be an intermolecular hydrogen bond formed between the polymer according to the embodiment of the present invention and 8OHdG. That is, it is conceivable that an amino group and a carbonyl group in a partial structure represented by any one of the general formulae 6 to 11, which is the structure of B forming the polymer represented by the general formula 1, are properly immobilized onto the surface of the polymer solid, and the groups form intermolecular hydrogen bonds with, for example, an amino group, a pyrimidine ring nitrogen atom, an imidazolinone ring nitrogen atom, a carbonyl group, and a hydroxy group in 8OHdG at a plurality of sites to recognize the 8OHdG molecule.

At the time of the design of the polymer capable of recognizing 8OHdG, when the polymer is designed so that the number of intermolecular hydrogen bonds to be formed may be 1 or 2, the polymer recognizes any other compound similar in structure to 8OHdG as typified by uric acid present in a large amount in a living organism, and hence its specific selectivity for 8OHdG reduces. Meanwhile, when the polymer is designed so that the number of intermolecular hydrogen bonding sites may be 4 or more, the polymer inevitably has a complicated molecular structure for securing an arrangement, a distance, and an angle for forming a proper intermolecular hydrogen bond. Such polymer is difficult to synthesize or the synthesis is extremely costly.

In the embodiment of the present invention, one or two hydrogen bonding sites in the partial structure represented by any one of the general formulae 6 to 11 are continuously or discontinuously arranged in the polymer, and when the sites are properly immobilized onto the surface of the polymer solid, the polymer behaves as if the polymer were identical to a complicated compound having four or more hydrogen bonding sites, thereby solving both the above-mentioned problems in terms of the specific selectivity and the cost. In addition, the polymer according to this embodiment may also provide the same effect in, for example, 8-oxo-guanosine or deoxyguanosine having a guanine skeleton similar to that of 8-oxo-deoxyguanosine (8OHdG). In this specification, compounds including those in which the same effect may be obtained are described as "8OHdG" in some cases.

The polymer according to this embodiment can be used as a bonding member (adsorbing member) that can be selectively bonded to 8OHdG or a similar marker in a solvent.

<Polymerizable Monomer>

The polymer in the embodiment of the present invention may be any one of a so-called homopolymer synthesized by the polymerization of a single monomer and a so-called copolymer synthesized by the polymerization of a plurality of kinds of monomers. In the homopolymer, however, sufficient sensitivity and sufficient specificity cannot be exhibited in some cases because the hydrogen bonding sites involved in molecular recognition are excessively present and are not properly immobilized onto the surface of the polymer solid, and hence the polymer misrecognizes a molecule except 8OHdG.

Accordingly, the polymer according to the embodiment of the present invention may be preferably a copolymer having, in addition to a repetition structure (molecular recognition unit) having a high molecular recognition ability, the structure having linked thereto a hydrogen bonding site having high specificity for 8OHdG, that is, the structure having B (sometimes referred to as "molecular recognition site"), a repetition structure (low recognition unit) that has low specificity for 8OHdG and hence does not contribute to any molecular recognition. The low recognition unit having low specificity for 8OHdG is, for example, a structure in which a group to be bonded to the position represented by * in any one of the general formulae 2 to 5 in the general formula 1 is not L but a hydrogen atom, an alkyl group, an aryl group, a heteroaryl group, an aralkyl group, or an acyl group.

Examples of the low recognition unit may include repetition structures represented by the following general formulae 32 to 35.

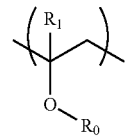

32

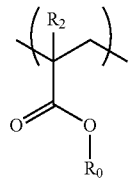

33

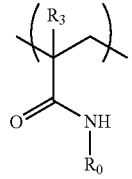

34

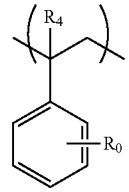

35

In the general formulae 32 to 35, $R_0$ represents any one of a hydrogen atom, an alkyl group, an aryl group, a heteroaryl group, an aralkyl group, and an acyl group, and $R_1$ to $R_4$ each independently represent a hydrogen atom or a methyl group.

That is, a polymer further including a repetition structure represented by any one of the general formulae 32 to 35, the structure serving as a low recognition unit, in addition to the repetition structure represented by the general formula 1 may be given as a preferred example of the polymer according to this embodiment.

Specific examples of the low recognition unit may include structures each obtained by polymerizing a polymerizable monomer, such as vinyl alcohol, vinyl acetate, acrylic acid, methacrylic acid, methyl acrylate, methyl methacrylate, acrylamide, methacrylamide, N-isopropylacrylamide, styrene, or α-methylstyrene.

In view of sensitivity and specificity for the adsorption of 8OHdG, in the polymer according to this embodiment, a ratio between the molecular recognition unit and the low recognition unit is preferably from 0.1:99.9 to 70:30 (mol:mol), more preferably from 1:99 to 50:50 (mol:mol).

In addition, in the embodiment of the present invention, the polymer may be of a so-called random polymer form or may be of a block polymer form, but is preferably a random polymer in terms of cost.

<Crosslinked Body>

In addition, in the embodiment of the present invention, when each polymer or copolymer becomes a polymer having a crosslinked structure (crosslinked body), its specificity is improved. The crosslinked structure refers to a structure in which main chains are linked to each other, and is formed by polymerization in the presence of monomers including two or more kinds of polymerizable monomers.

A polymer further including a repetition structure represented by the following general formula 26, in addition to the repetition structure represented by the general formula 1 may be given as an example of the crosslinked body.

26

$L_0$ in the general formula 26 represents a divalent group serving as a crosslinked structure together with $L_0$ of another repetition structure, and

is represented by any one of the following general formulae 2 to 5:

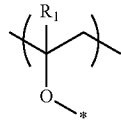

2

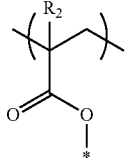

3

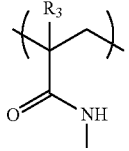

4

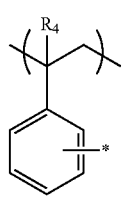

5 in the general formulae 2 to 5, $R_1$ to $R_4$ each independently represent a hydrogen atom or a methyl group, and * represents a bonding position with $L_0$.

Specifically, the skeleton of the crosslinked body may be obtained by polymerizing a polyvalent polymerizable monomer, such as ethylene glycol dimethacrylate, diethylene glycol dimethacrylate, neopentyl glycol dimethacrylate, 1,6-hexanediol diacrylate, divinylbenzene, trimethylolpropane trimethacrylate, or pentaerythritol tetraacrylate.

The improvement in specificity is considered to be because of the following reason: when the polymer has the crosslinked structure in itself, the steric structure of a hydrogen bonding site involved in molecular recognition is further immobilized, and hence the desorption of 8OHdG that has been captured once is suppressed. However, details about the improvement are unclear. In the crosslinked body according to the embodiment of the present invention, a ratio between the numbers of repetition of a repetition structure free of any crosslinked structure and a repetition structure including the crosslinked structure is preferably from 0.1:99.9 to 90:10 (mol:mol), and is more preferably from 10:90 to 50:50 (mol:mol) in order that a stronger bond may be obtained through an improvement in polymerization ratio.

<Template Molecule>

The polymer according to the embodiment of the present invention is obtained by using a compound represented by the following general formula 24 as a so-called template material and polymerizing the polymerizable monomer in the presence of the compound:

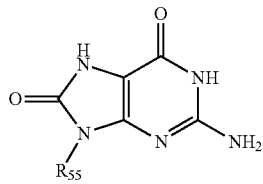

24

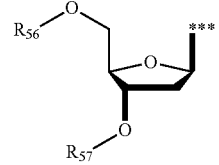

25 provided that in the general formula 24, $R_{55}$ represents an alkyl group having 1 to 18 carbon atoms, an aryl group, a heteroaryl group, an aralkyl group, or a structure represented by the general formula 25, and in the general formula 25, $R_{56}$ and $R_{57}$ each independently represent a hydrogen atom, an alkyl group having 1 to 18 carbon atoms, an aryl group, an acyl group, or a silyl group, and *** represents a bonding position with a nitrogen atom in the general formula 24.

The compound represented by the general formula 24 in which $R_{55}$ represents a structure represented by the general formula 25, and $R_{56}$ and $R_{57}$ each represent a hydrogen atom is 8OHdG represented by the structural formula C.

8OHdG itself is most suitable as a template molecule for obtaining a polymer capable of adsorbing 8OHdG with high sensitivity and specifically, but 8OHdG has extremely low solubility in an organic solvent. In order to perform the polymerization reaction of the various polymerizable monomers, the template molecule needs to be dissolved in the organic solvent together with the various polymerizable monomers, or the template molecule needs to be directly dissolved in the various polymerizable monomers. A compound having such structure as represented by the general formula 24 is preferred as the template molecule because the compound forms the same intermolecular hydrogen bond as that of 8OHdG between itself and the molecular recognition unit in the polymer, and can be dissolved in the organic solvent.

<Substituent>

Substituents in the general formulae in this specification are described below.

The halogen atom is, for example, a fluorine atom, a chlorine atom, a bromine atom, or an iodine atom.

The alkyl group is, for example, a linear, branched, or cyclic alkyl group having 1 to 12 carbon atoms. The alkyl group may have a substituent to the extent that the sensitivity and specificity of the polymer according to the embodiment of the present invention for 8OHdG are not impaired. Examples of such substituent include: halogen atoms, such as a fluorine atom, a chlorine atom, and a bromine atom; alkoxy groups each having 1 to 6 carbon atoms, such as a methoxy group, an ethoxy group, a propoxy group, and a butoxy group; a hydroxy group; an amino group; a cyano group; a sulfo group; and a carboxyl group. Examples of the alkyl group also including the one having the substituent include: unsubstituted alkyl groups, such as a methyl group, an ethyl group, a propyl group, an isopropyl group, a butyl group, an isobutyl group, a sec-butyl group, a tert-butyl group, a pentyl group, an isopentyl group, a sec-pentyl group, a tert-pentyl group, a neopentyl group, a hexyl group, a heptyl group, an octyl group, a 2-ethylhexyl group, and a dodecyl group; substituted alkyl groups, such as a trifluoromethyl group, a 2-methoxyethyl group, a 1-hydroxyethyl group, a 1-aminoethyl group, a 2-cyanoethyl group, a 3-sulfopropyl group, and a 3-carboxypropyl group; unsubstituted cycloalkyl groups, such as a cyclopropyl group, a cyclobutyl group, a cyclopentyl group, a cyclohexyl group, a cycloheptyl group, a cyclooctyl group, a decahydronaphthyl group, an adamantyl group, and a decahydroacenaphthylenyl group; and substituted cycloalkyl groups, such as a 2-chlorocyclohexyl group, a 2-methylcyclohexyl group, a 3-methylcyclohexyl group, a 4-methylcyclohexyl group, a 2,6-dimethylcyclohexyl group, a 2,4,6-trimethylcyclohexyl group, a 4-methoxycyclohexyl group, a 2-hydroxycyclohexyl group, a 2-aminocyclohexyl group, a 3-cyanocyclohexyl group, a 3-sulfocyclohexyl group, and a 2-carboxycyclohexyl group.

Examples of the aryl group include aryl groups each having 6 to 10 carbon atoms. The aryl group may have a substituent to the extent that the sensitivity and specificity of the polymer according to the embodiment of the present invention for 8OHdG are not impaired. Examples of such substituent include: halogen atoms, such as a fluorine atom, a chlorine atom, and a bromine atom; alkyl groups each having 1 to 6 carbon atoms, such as a methyl group, an ethyl group, a propyl group, an isopropyl group, a butyl group, and a tert-butyl group; alkoxy groups each having 1 to 6 carbon atoms, such as a methoxy group, an ethoxy group, a propoxy group, and a butoxy group; a hydroxy group; an amino group; a cyano group; a sulfo group; and a carboxyl group. Examples of the aryl group also including the one having the substituent include: unsubstituted aryl groups, such as a phenyl group, a 1-naphthyl group, and a 2-naphthyl group; and substituted aryl groups, such as an o-chlorophenyl group, an o-tolyl group, a m-tolyl group, a p-tolyl group, a 2,6-dimethylphenyl group, a 2,4,6-trimethylphenyl group, a p-methoxyphenyl group, an o-aminophenyl group, an o-hydroxyphenyl group, a m-cyanophenyl group, a m-sulfophenyl group, an o-carboxyphenyl group, a 2-hydroxy-1-naphthyl group, and a 1-hydroxy-2-naphthyl group.

Examples of the heteroaryl group include aryl groups each having 3 to 10 carbon atoms. The heteroaryl group may have a substituent to the extent that the sensitivity and specificity of the polymer according to the embodiment of the present invention for 8OHdG are not impaired. Examples of such substituent include: halogen atoms, such as a fluorine atom, a chlorine atom, and a bromine atom; alkyl groups each having 1 to 6 carbon atoms, such as a methyl group, an ethyl group, a propyl group, an isopropyl group, a butyl group, and a tert-butyl group; alkoxy groups each having 1 to 6 carbon atoms, such as a methoxy group, an ethoxy group, a propoxy group, and a butoxy group; a hydroxy group; an amino group; a cyano group; a sulfo group; and a carboxyl group. Examples of the heteroaryl group also including the one having the substituent include: unsubstituted heteroaryl groups, such as a 2-pyridyl group, a 3-pyrazolyl group, a 2-imidazolyl group, a 2-thienyl group, a 2-furyl group, a 2-thiazolyl group, a 3-pyrryl group, a 3-indolyl group, and a 1-carbazolyl group; and substituted heteroaryl groups, such as a 5-chloro-2-pyridyl group, a 4-methyl-3-pyrazolyl group, a 1-ethyl-3-methyl-2-imidazolyl group, a 5-phenyl-2-thienyl group, a 5-methoxy-2-furyl group, a 4-amino-2-thiazolyl group, a 1-phenyl-3-pyrryl group, a 2-phenyl-1-indolyl group, and a 3-nitro-1-carbazolyl group.

Examples of the aralkyl group include aralkyl groups each having 7 to 12 carbon atoms. The aralkyl group may have a substituent to the extent that the sensitivity and specificity of the polymer according to the embodiment of the present invention for 8OHdG are not impaired. Examples of such substituent include: halogen atoms, such as a fluorine atom, a chlorine atom, and a bromine atom; alkyl groups each having 1 to 6 carbon atoms, such as a methyl group, an ethyl group, a propyl group, an isopropyl group, a butyl group, and a tert-butyl group; alkoxy groups each having 1 to 6 carbon atoms, such as a methoxy group, an ethoxy group, a propoxy group, and a butoxy group; a hydroxy group; an amino group; a nitro group; a sulfo group; and a carboxyl group. Examples of the aralkyl group also including the one having the substituent include: unsubstituted aralkyl groups, such as a benzyl group, a 2-phenethyl group, and a 2-(1-naphthyl)ethyl group; and substituted aralkyl groups, such as a 4-bromobenzyl group, a 2-(3-fluorophenyl)ethyl group, a 2-methylbenzyl group, a 3,5-dimethoxybenzyl group, a 3,5-dihydroxybenzyl group, a 2-nitrobenzyl group, a 3-sulfobenzyl group, a 2-carboxybenzyl group, and a 3-carboxybenzyl group.

Examples of the amino group include unsubstituted amino groups and substituted amino groups. A substituent may be selected to the extent that the sensitivity and specificity of the polymer according to the embodiment of the present invention for 8OHdG are not impaired. Examples of such substituent include: alkyl groups each having 1 to 12 carbon atoms, such as a methyl group, an ethyl group, a propyl group, an isopropyl group, a butyl group, a tert-butyl group, and a dodecyl group; alkenyl groups each having 2 to 12 carbon atoms, such as a vinyl group, a 1-propenyl group, a 2-propenyl group, a 1-butenyl group, a 2-butenyl group, and a 1-dodecenyl group; aryl groups each having 6 to 10 carbon atoms, such as a phenyl group, a 1-naphthyl group, and a 2-naphthyl group; aralkyl groups each having 7 to 12 carbon atoms, such as a benzyl group, a 2-phenethyl group, and a 2-(1-naphthyl)ethyl group; a sulfo group; and a carboxyl group. Each of those substituents may further have a substituent to the extent that the sensitivity and specificity of the polymer according to the embodiment of the present invention for 8OHdG are not impaired. Examples of such substituent include: halogen atoms, such as a fluorine atom, a chlorine atom, and a bromine atom; alkoxy groups each having 1 to 6 carbon atoms, such as a methoxy group, an ethoxy group, a propoxy group, and a butoxy group; a hydroxy group; a nitro group; a cyano group; a sulfo group; and a carboxyl group.

Examples of the substituted amino groups include a methylamino group, a dimethylamino group, a diethylamino group, a dibutylamino group, a 2-ethylhexylamino group, a dodecylamino group, a 2,2,2-trifluoroethylamino group, a 2,2-dimethoxyethylamino group, a 2-hydroxyethylamino group, a 2-nitroethylamino group, a 2-cyanoethyl group, a 2-sulfoethylamino group, a 2-carboxyethylamino group, a vinylamino group, a 2-propenylamino group, an anilino group, a diphenylamino group, a benzylamino group, an N-sulfamate group, and an N-carbamate group.

Examples of the acyl group include linear or branched hydrocarbon-based acyl groups each having 1 to 12 carbon atoms and aromatic acyl groups each having 7 to 13 carbon atoms. The acyl group may have a substituent to the extent that the sensitivity and specificity of the polymer according to the embodiment of the present invention for 8OHdG are not impaired. Examples of such substituent include: halogen atoms, such as a fluorine atom, a chlorine atom, and a bromine atom; alkoxy groups each having 1 to 6 carbon atoms, such as a methoxy group, an ethoxy group, a propoxy group, and a butoxy group; a hydroxy group; a nitro group; a cyano group; a sulfo group; and a carboxyl group. Examples of the acyl group also including the one having the substituent include: unsubstituted acyl groups, such as a methanoyl group, an ethanoyl group, a propanoyl group, a butanoyl group, an isobutanoyl group, a pentanoyl group, a hexanoyl group, a dodecanoyl group, a propenoyl group, a 2-methylpropenoyl group, a benzoyl group, and a 2-naphthoyl group; and substituted acyl groups, such as a 2,2,2-trifluoroethanoyl group, a 2,2-dimethoxyethanoyl group, a 2-hydroxyethanoyl group, a 2-nitroethanoyl group, a 2-cyanoethanoyl group, a 3-carboxypropanoyl group, and a 2-sulfobenzoyl group.

Examples of the silyl group include silyl groups each having 3 to 16 carbon atoms. The silyl group may have a substituent to the extent that the sensitivity and specificity of the polymer according to the embodiment of the present invention for 8OHdG are not impaired. Examples of such substituent include: halogen atoms, such as a fluorine atom, a chlorine atom, and a bromine atom; alkyl groups each having 1 to 6 carbon atoms, such as a methyl group, an ethyl group, a propyl group, an isopropyl group, a butyl group, and a tert-butyl group; alkoxy groups each having 1 to 6 carbon atoms, such as a methoxy group, an ethoxy group, a propoxy group, and a butoxy group; a hydroxy group; an amino group; a nitro group; a sulfo group; and a carboxyl group. Examples of the silyl group also including the one having the substituent include silyl groups, such as a trimethylsilyl group, a triisopropylsilyl group, a tert-butyldimethylsilyl group, a tert-butyldiphenylsilyl group, a 2-hydroxyethoxydimethylsilyl group, and 3-aminopropoxydiphenylsilyl group.

Specific Examples of A

Preferred specific examples of the structure of

in the general formula 1 or 26 in the embodiment of the present invention are shown in the following formulae 201-p to 502-p. However, the structure is not limited to the following examples. In each of the formulae 201-p to 502-p, * represents a bonding position with L in each structural formula.

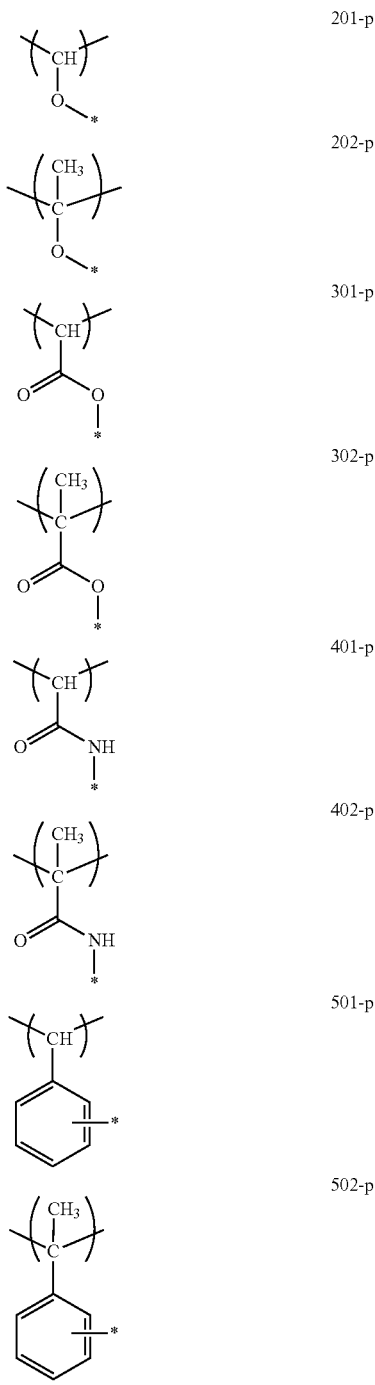

Preferred specific examples of polymerizable monomers forming the respective structures represented by the formulae 201-p to 502-p are shown in the following formulae 201 to 502. However, the structure is not limited to the following examples. * represents a bonding position with L in each structural formula.

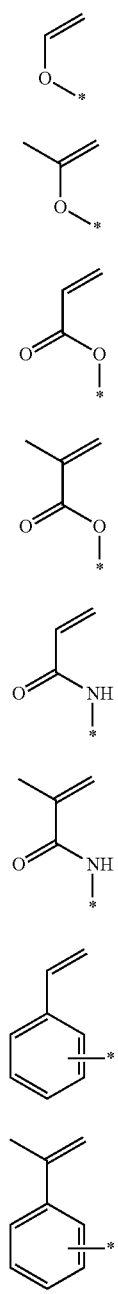
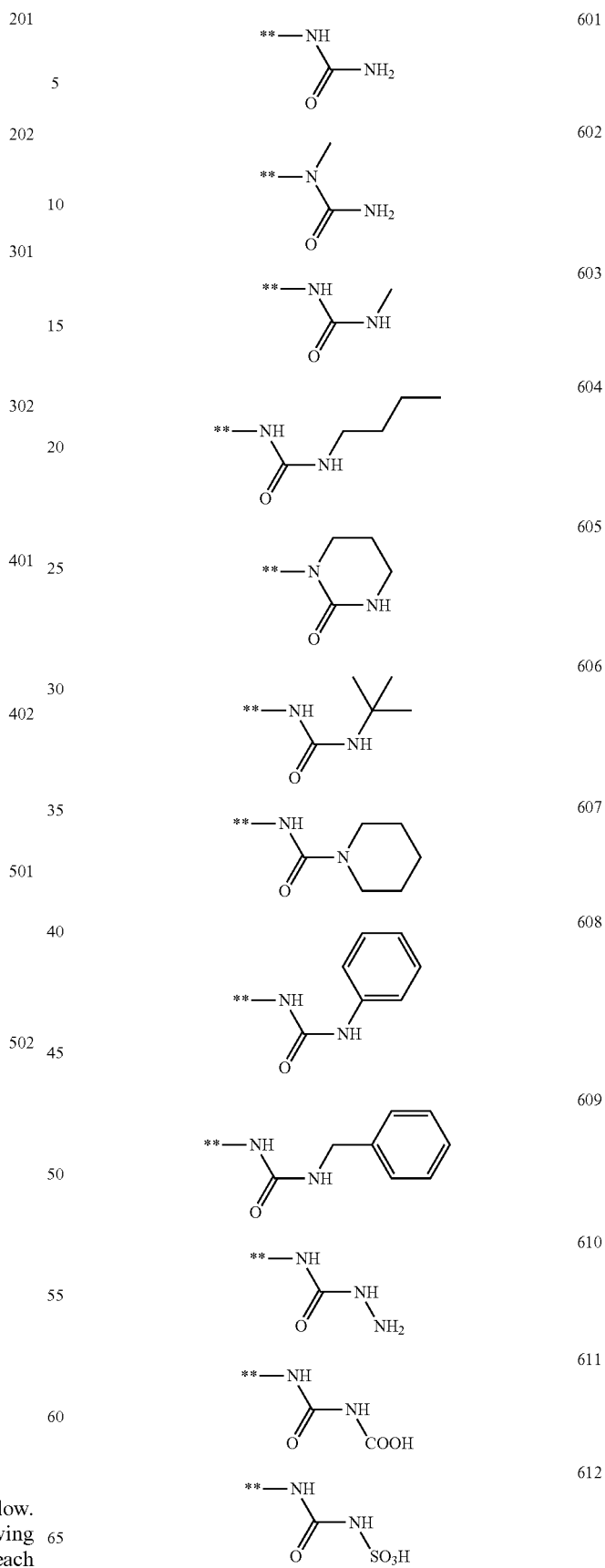
Specific Examples of B
Preferred specific examples of the structure of
|
B
in the embodiment of the present invention are shown below. However, the structure is not limited to the following examples. ** represents a bonding position with L in each structural formula.

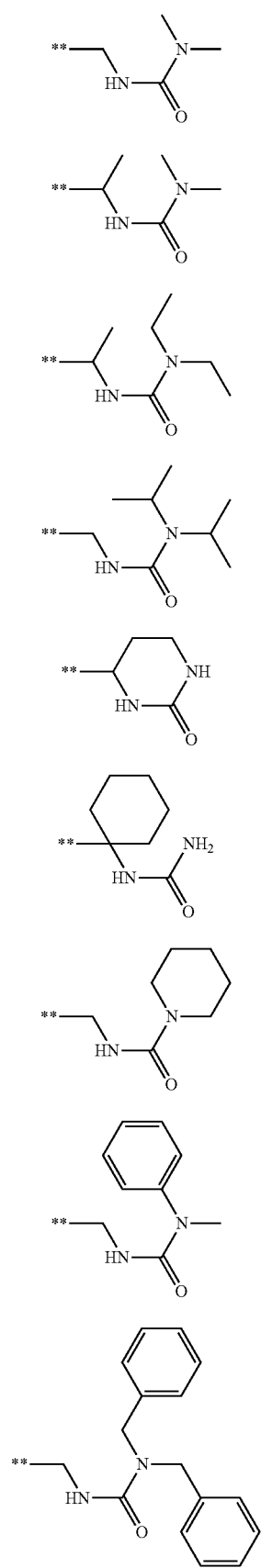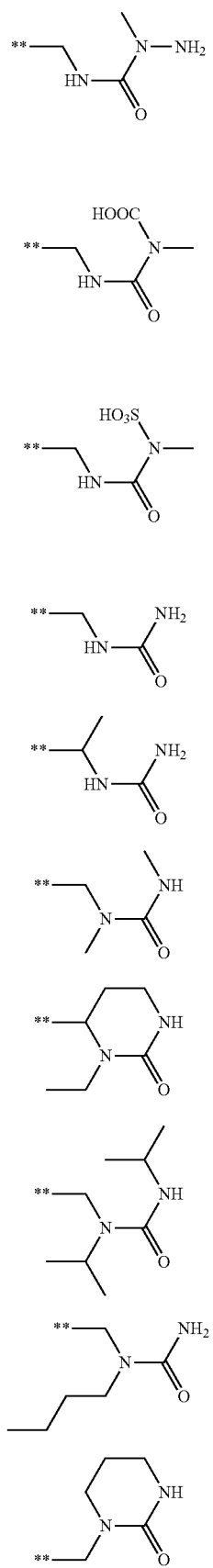

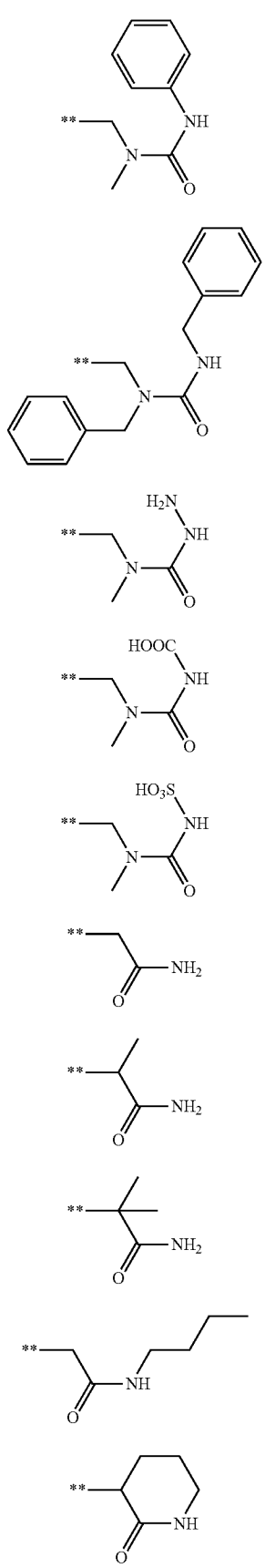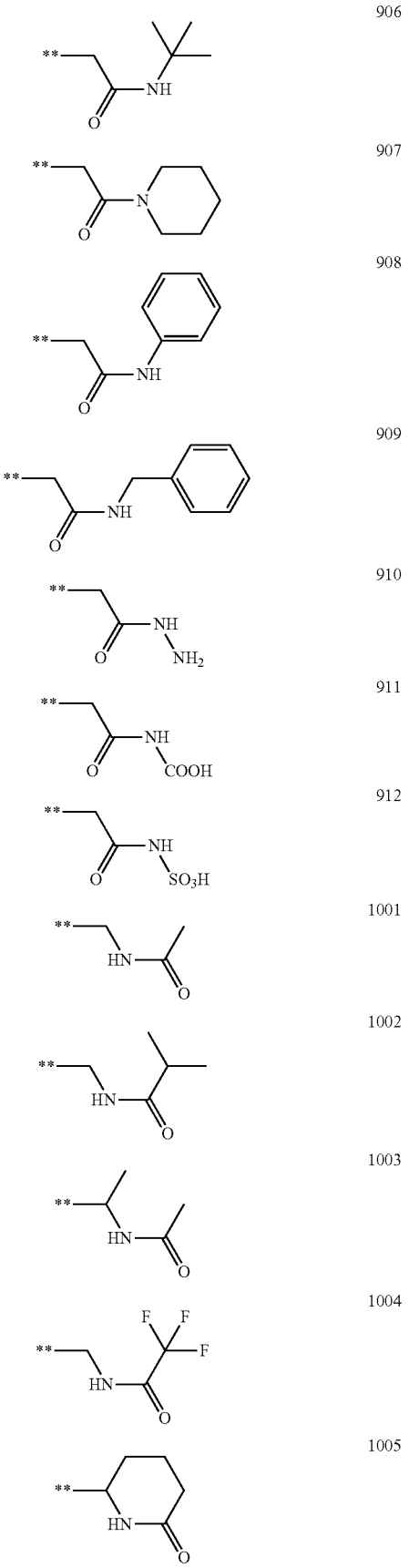

| | |
|---|---|
| 1006 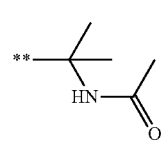 | 1104 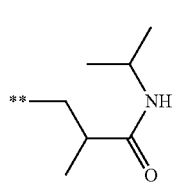 |
| 1007 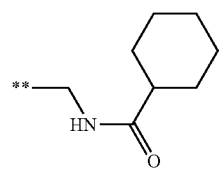 | 1105 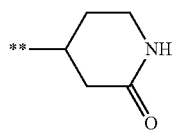 |
| 1008 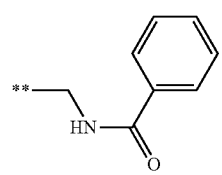 | 1106 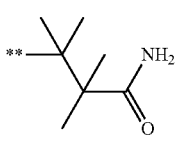 |
| 1009 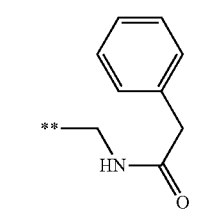 | 1107 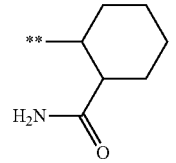 |
| 1010 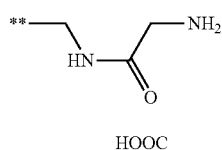 | 1108 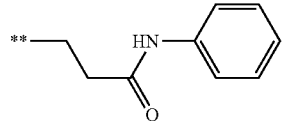 |
| 1011 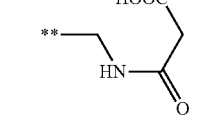 | 1109 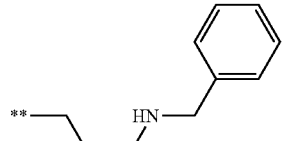 |
| 1012 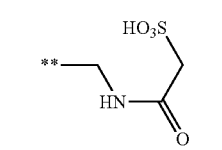 | 1110 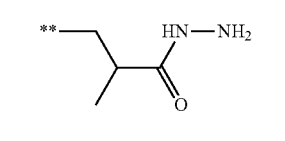 |
| 1101 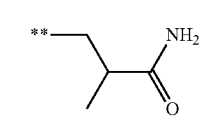 | 1111 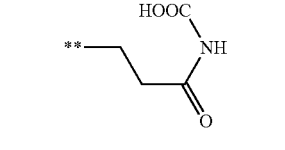 |
| 1102 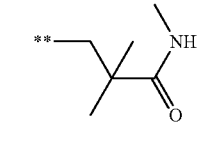 | 1112 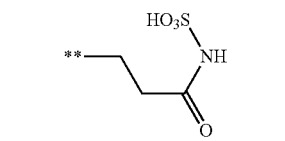 |
| 1103 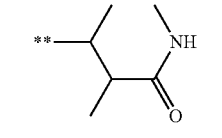 | 1201 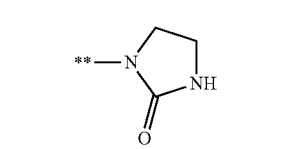 |

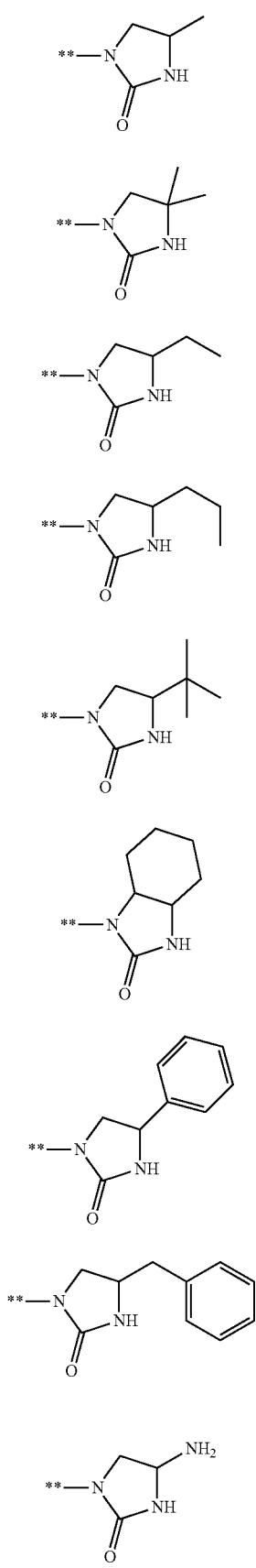
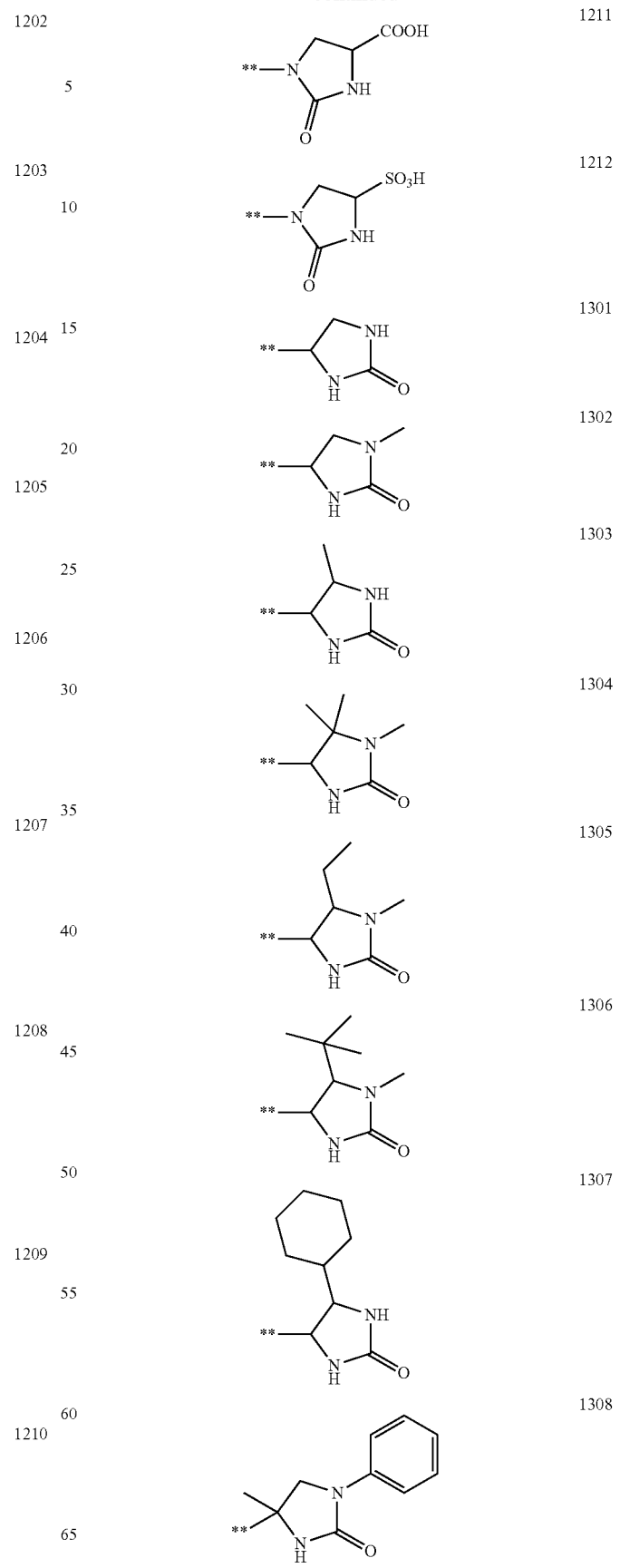

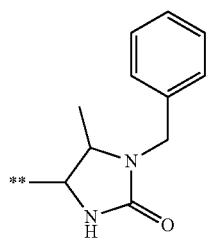 1309
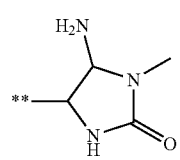 1310
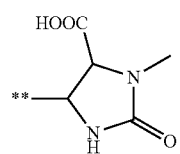 1311
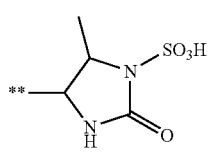 1312
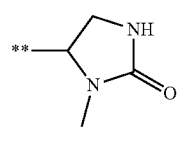 1401
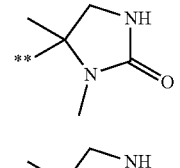 1402
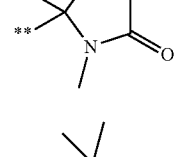 1403
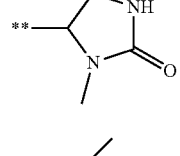 1404
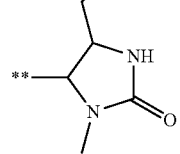 1405
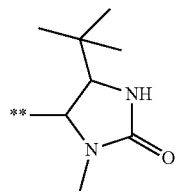 1406
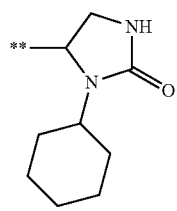 1407
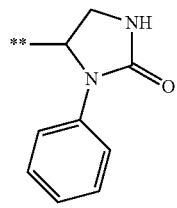 1408
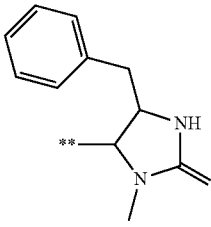 1409
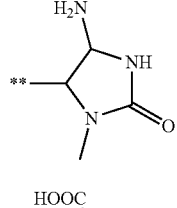 1410
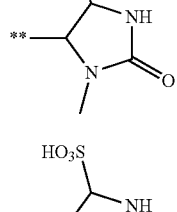 1411
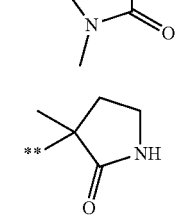 1412
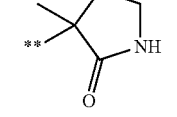 1501

1502
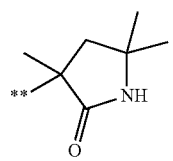
1503
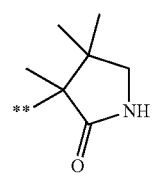
1504
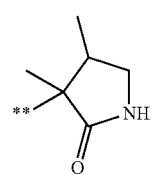
1505
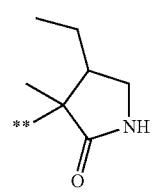
1506
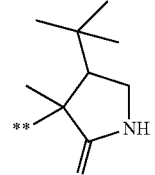
1507
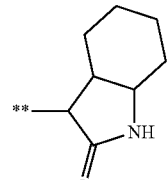
1508
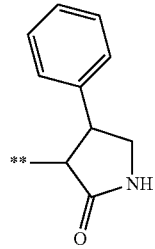
1509
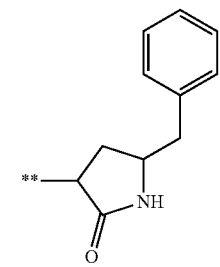
1510
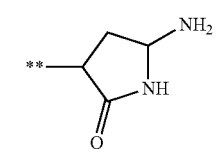
1511
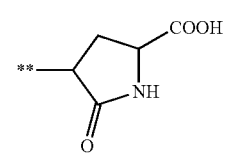
1512
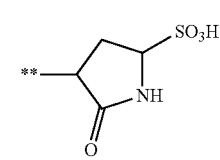
1601
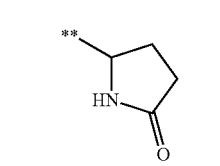
1602
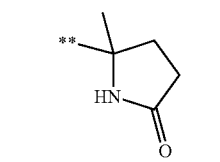
1603
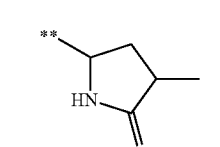
1604
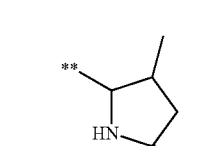
1605
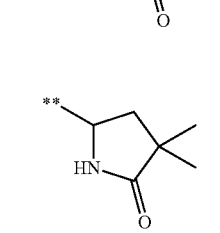

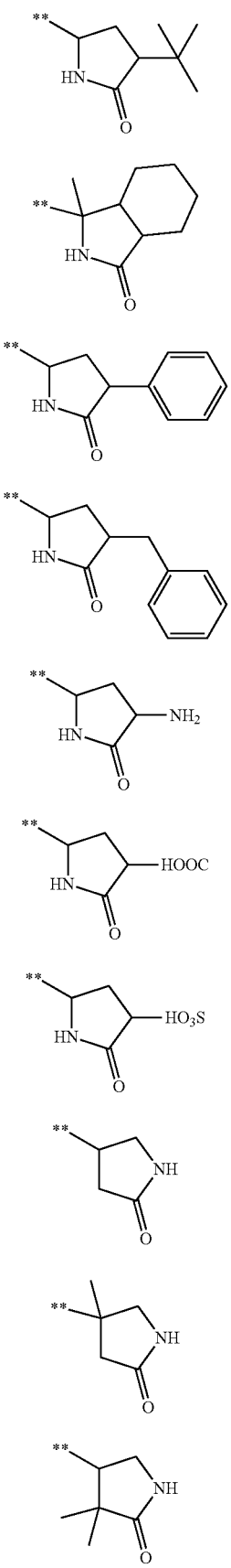
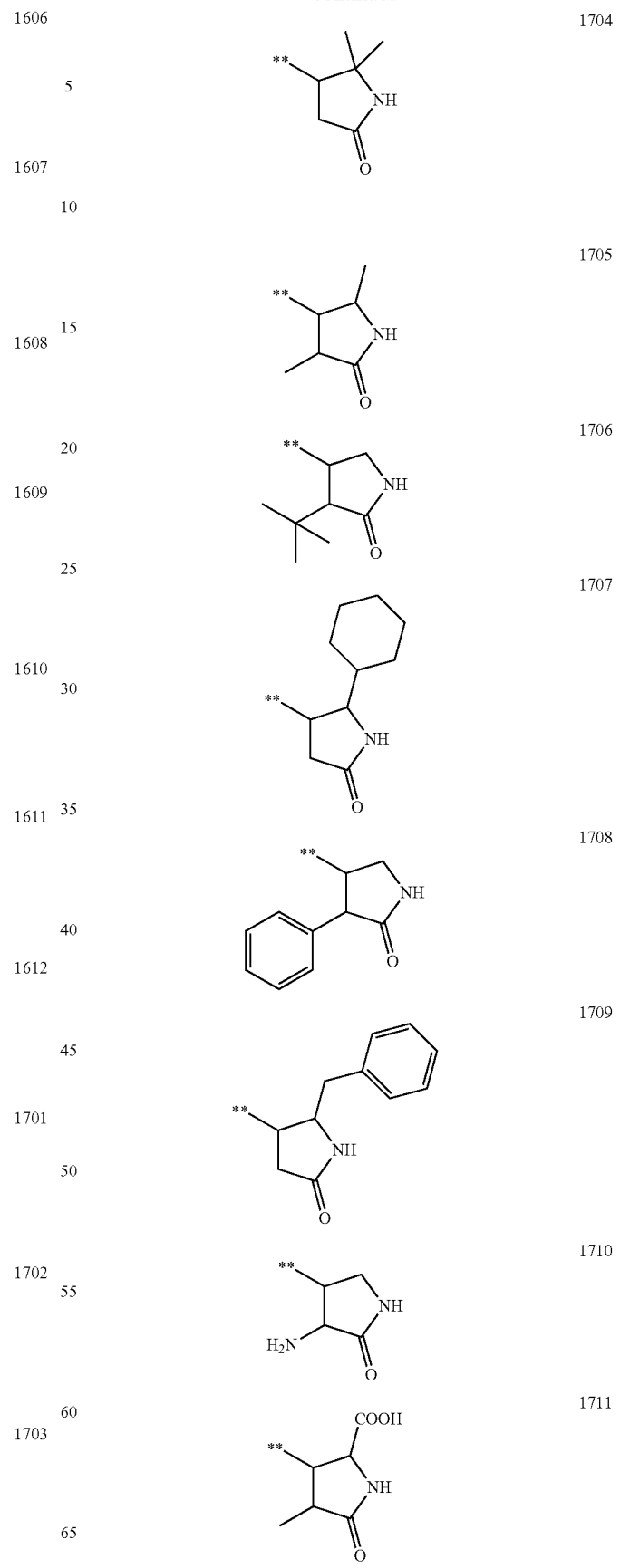

Specific Examples of L

Preferred specific examples of the structure of L in the embodiment of the present invention are shown below. However, the structure is not limited to the following examples. * represents a bonding position with A in each structural formula, and ** represents a bonding position with B in each structural formula.

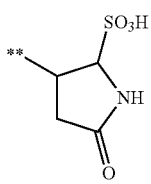
1712

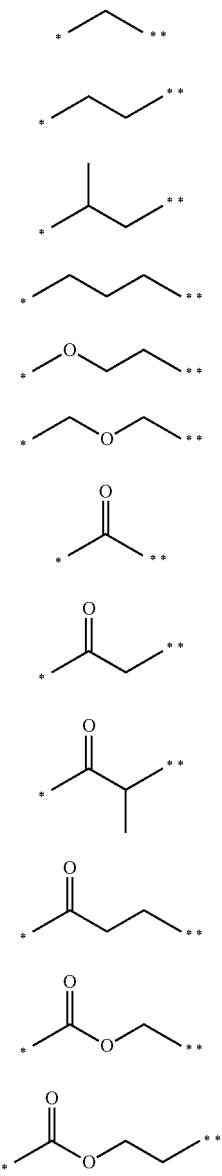

2601
2602
2603
2604
2605
2606
2607
2608
2609
2610
2611
2612

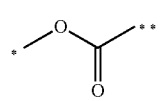

2613
2614
2615
2616
2617
2618
2619
2620
2621
2622
2623
2624

A method of representing each of the polymerizable monomers of the present invention to be used in Examples below is based on the following. That is, for example, when the structural formula 301 is selected as the structure of the polymerizable monomer of the repetition unit A in the general formula 1, the structural formula 2601 is selected as the linking group L therein, and the structural formula 1201 is selected as B serving as the molecular recognition site therein, the polymer of the present invention is represented like "Compound 301-2601-1201."

Specific Examples of Template Molecule

Preferred specific examples of the compound represented by the general formula 24 in the embodiment of the present invention are shown below. However, the compound is not limited to the following examples.
2401
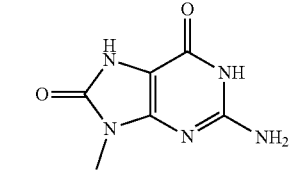
2402
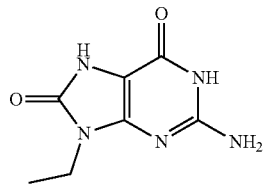
2403
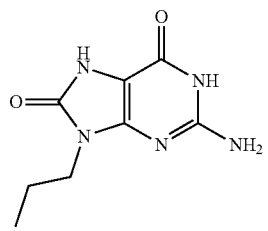
2404
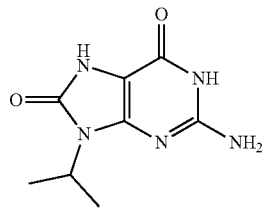
2405
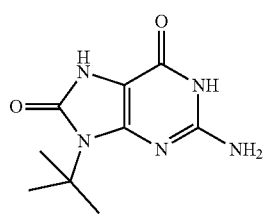
2406
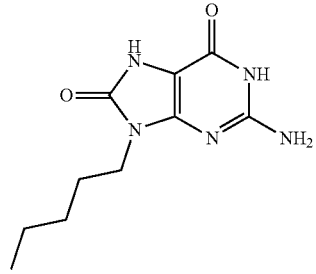
2407
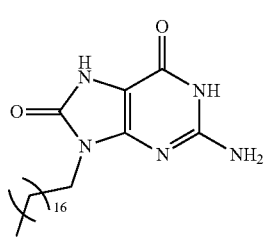
-continued
2408
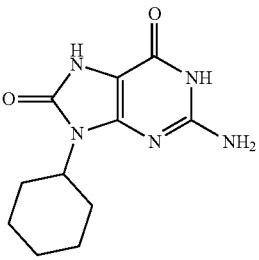
2409
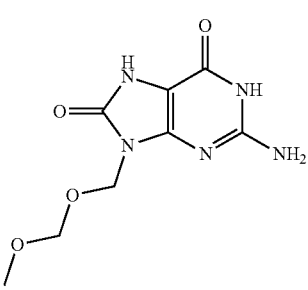
2410
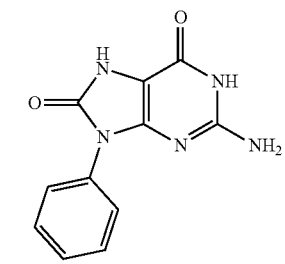
2411
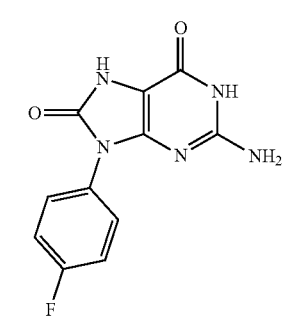
2412
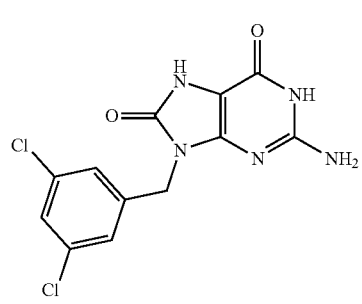

| | |
|---|---|
| 2413 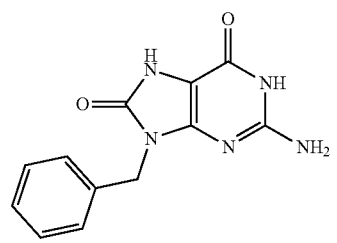 | 2419 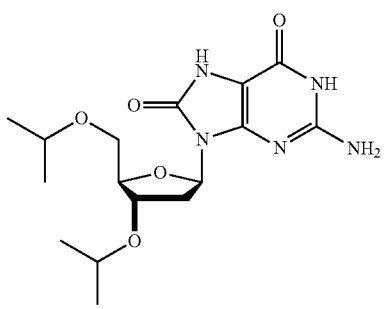 |
| 2414 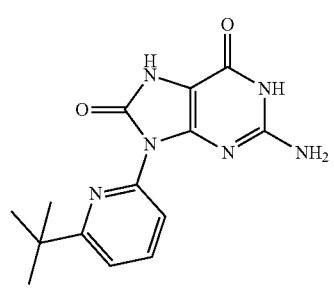 | 2420 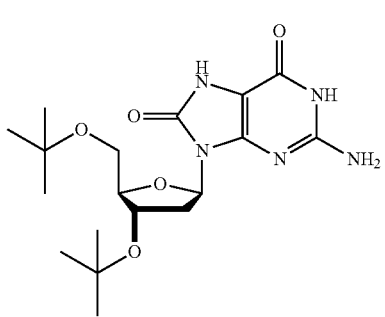 |
| 2415 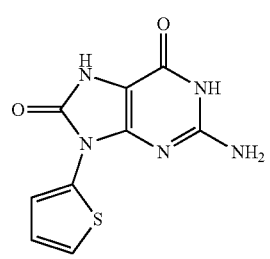 | 2421 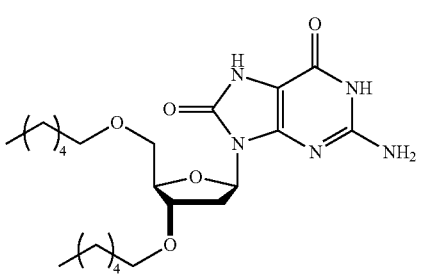 |
| 2416 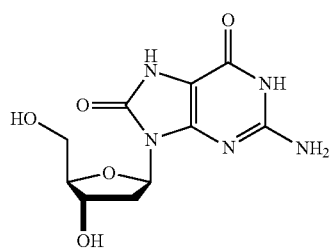 | 2422 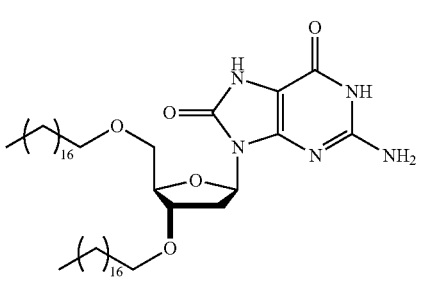 |
| 2417 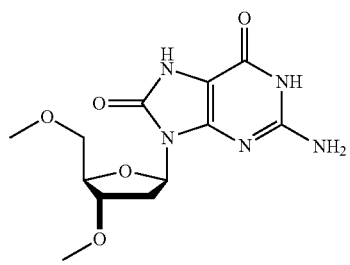 | 2423 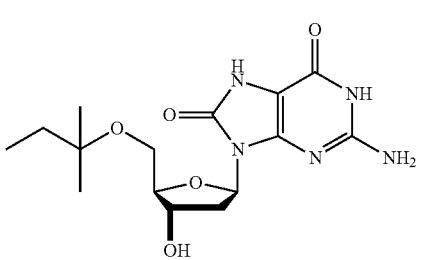 |
| 2418 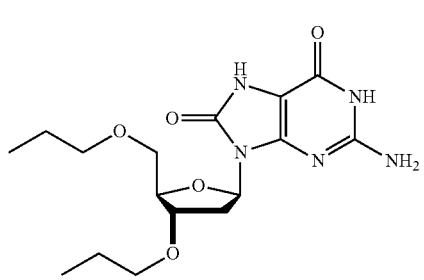 | |

2424
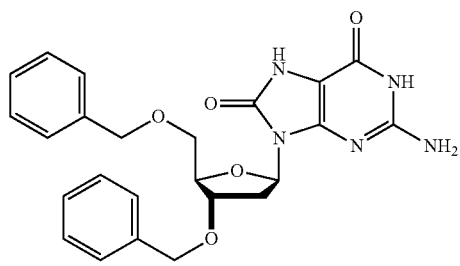
2425
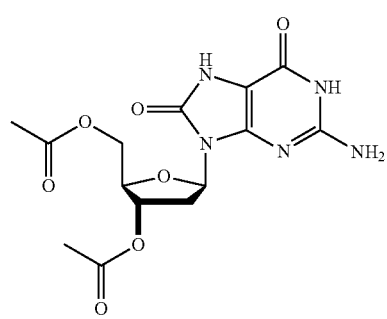
2426
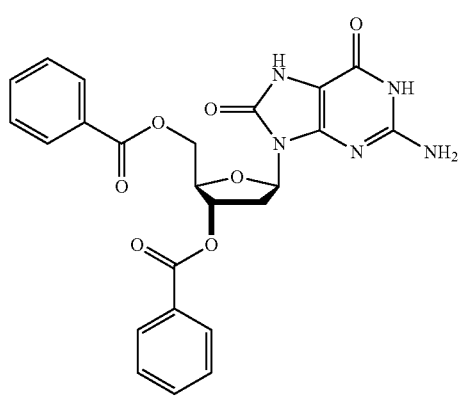
2427
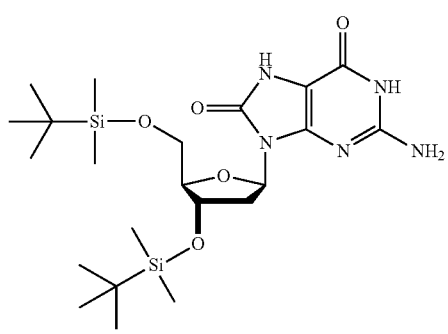
2428
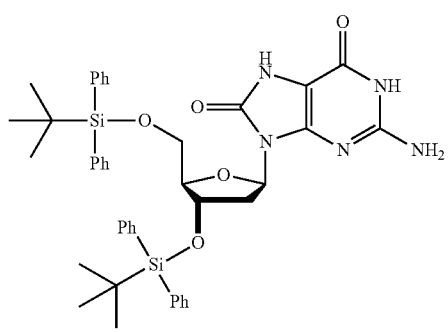
2429
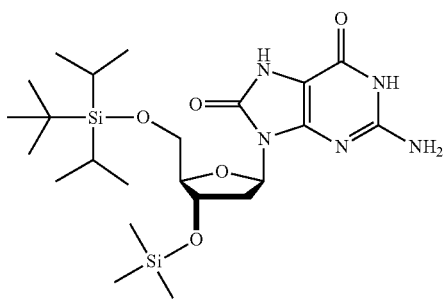
2430
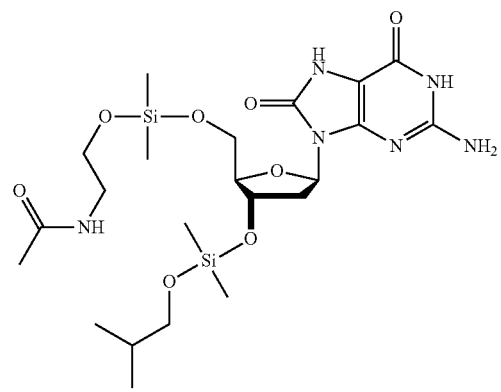
2431
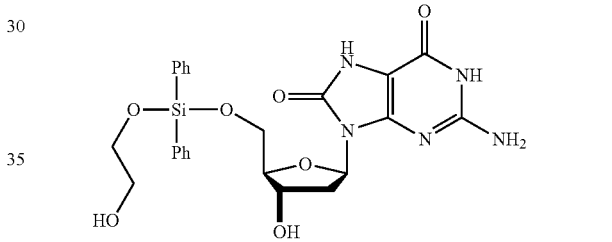
Embodiment Based on Production Method
In addition, a polymer obtained by polymerizing a compound represented by the following general formula 36 in the presence of a compound represented by the following general formula 24 may be given as an embodiment of the present invention:
24
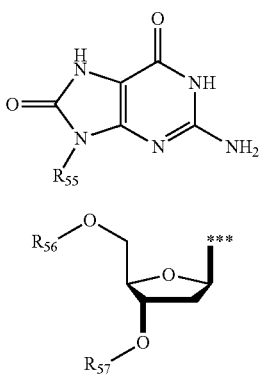
25 provided that in the general formula 24, $R_{55}$ represents an alkyl group having 1 to 18 carbon atoms, an aryl group, a heteroaryl group, an aralkyl group, or a structure represented by the general formula 25, and in the general formula 25, $R_{56}$ and $R_{57}$ each independently represent a hydrogen atom, an alkyl group having 1 to 18 carbon atoms, an aryl group, an acyl group, or a silyl group, and *** represents a bonding position with a nitrogen atom in the general formula 24:

36

$$\begin{array}{c} A_{mono} \\ | \\ L \\ | \\ B \end{array}$$

provided that in the general formula 36, $$\begin{array}{c} A_{mono} \\ | \end{array}$$

is represented by any one of the following general formulae 3002 to 3005, $$\begin{array}{c} | \\ B \end{array}$$

is represented by any one of the following general formulae 6 to 11, and

L represents a divalent linking group containing 1 to 3 carbon atoms for linking A and B:

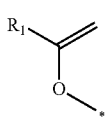
3002

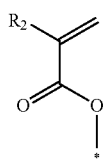
3003

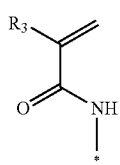
3004

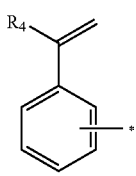
3005

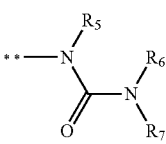
6

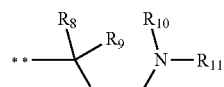
7

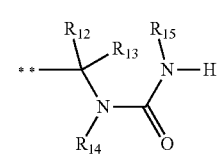
8

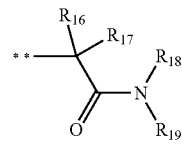
9

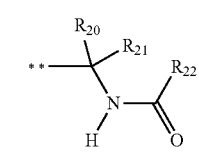
10

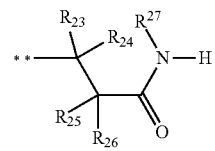
11 provided that in the general formulae 3002 to 3005, $R_1$ to $R_4$ each independently represent a hydrogen atom or a methyl group, and * represents a bonding position with L, and in the general formulae 6 to 11, $R_5$ to $R_{27}$ each independently represent any one of a hydrogen atom, a halogen atom, an alkyl group, an aryl group, a heteroaryl group, an aralkyl group, a hydroxy group, an amino group, a carboxyl group, a sulfo group, and a nitro group, $R_5$ and $R_6$, $R_6$ and $R_7$, $R_5$ and $R_9$, $R_9$ and $R_{10}$, $R_{10}$ and $R_{11}$, $R_{12}$ and $R_{13}$, $R_{13}$ and $R_{15}$, $R_{16}$ and $R_{17}$, $R_{17}$ and $R_{18}$, $R_{18}$ and $R_{19}$, $R_{20}$ and $R_{21}$, $R_{21}$ and $R_{22}$, $R_{23}$ and $R_{24}$, and $R_{24}$ and $R_{27}$ may each independently be bonded to each other to form a cyclic structure, and ** represents a bonding position with L.

Examples

Now, the present invention is more specifically described by way of Examples. However, the present invention is not limited to these Examples, and various modifications can be made without departing from the gist of the present invention.

<Synthesis of Polymer 1>

Compound 201-2601-601 (0.091 mmol) and vinyl acetate (0.122 mmol) serving as polymerizable monomers, and 1-hydroxycyclohexyl phenyl ketone (0.107 mmol) serving as an initiator were mixed, and then the mixture was irradiated with UV light (50 mW·cm$^{-2}$, 365 nm, irradiation distance: 123 mm) from a high-pressure mercury lamp "HANDY CURE LAB" (manufactured by SEN LIGHTS Corporation) in a stream of nitrogen for 3 hours to provide a target polymer 1.

<Synthesis of Polymer 2>

A target polymer 2 was obtained by the same method as that of the synthesis example of the polymer 1 except that Compound 201-2601-601 was changed to Compound 201-2608-608.

<Synthesis of Polymer 3>

A target polymer 3 was obtained by the same method as that of the synthesis example of the polymer 1 except that Compound 201-2601-601 was changed to Compound 202-2616-705.

<Synthesis of Polymer 4>

A target polymer 4 was obtained by the same method as that of the synthesis example of the polymer 1 except that: Compound 201-2601-601 was changed to Compound 301-2602-601; and vinyl acetate was changed to methyl acrylate.

<Synthesis of Polymer 5>

A target polymer 5 was obtained by the same method as that of the synthesis example of the polymer 4 except that Compound 301-2602-601 was changed to Compound 301-2616-809.

<Synthesis of Polymer 6>

Compound 401-2616-901 (0.091 mmol) and methyl acrylate (0.122 mmol) serving as polymerizable monomers, ethylene glycol dimethacrylate (1.113 mmol) serving as a crosslinking agent, and 1-hydroxycyclohexyl phenyl ketone (0.107 mmol) serving as an initiator were mixed, and then the mixture was irradiated with UV light (50 mW·cm$^{-2}$, 365 nm, irradiation distance: 123 mm) from a high-pressure mercury lamp "HANDY CURE LAB" (manufactured by SEN LIGHTS Corporation) in a stream of nitrogen for 3 hours to provide a target polymer 6.

<Synthesis of Polymer 7>

A target polymer 7 was obtained by the same method as that of the synthesis example of the polymer 6 except that: Compound 401-2616-901 was changed to Compound 402-2616-1004; and methyl acrylate was not loaded.

<Synthesis of Polymer 8>

A target polymer 8 was obtained by the same method as that of the synthesis example of the polymer 7 except that Compound 402-2616-1004 was changed to Compound 301-2602-1111.

<Synthesis of Polymer 9>

Compound 301-2602-1111 (0.091 mmol) serving as a polymerizable monomer, 1-hydroxycyclohexyl phenyl ketone (0.107 mmol) serving as an initiator, and 3.50 ml of chloroform serving as a solvent were mixed, and then the mixture was irradiated with UV light (50 mW·cm$^{-2}$, 365 nm, irradiation distance: 123 mm) from a high-pressure mercury lamp "HANDY CURE LAB" (manufactured by SEN LIGHTS Corporation) in a stream of nitrogen for 3 hours to provide a target polymer 9.

<Synthesis of Polymer 10>

A target polymer 10 was obtained by the same method as that of the synthesis example of the polymer 9 except that acrylamide (0.122 mmol) was added as a polymerizable monomer.

<Synthesis of Polymer 11>

A target polymer 11 was obtained by the same method as that of the synthesis example of the polymer 10 except that Compound 301-2602-1111 was changed to Compound 301-2602-1201.

<Synthesis of Polymer 12>

A target polymer 12 was obtained by the same method as that of the synthesis example of the polymer 11 except that acrylamide was changed to methacrylamide.

<Synthesis of Polymer 13>

A target polymer 13 was obtained by the same method as that of the synthesis example of the polymer 11 except that acrylamide was changed to acrylic acid.

<Synthesis of Polymer 14>

A target polymer 14 was obtained by the same method as that of the synthesis example of the polymer 11 except that acrylamide was changed to methacrylic acid.

<Synthesis of Polymer 15>

A target polymer 15 was obtained by the same method as that of the synthesis example of the polymer 11 except that acrylamide was changed to N-isopropylacrylamide.

<Synthesis of Polymer 16>

A target polymer 16 was obtained by the same method as that of the synthesis example of the polymer 14 except that Compound 301-2602-1201 was changed to Compound 401-2602-1201.

<Synthesis of Polymer 17>

A target polymer 17 was obtained by the same method as that of the synthesis example of the polymer 16 except that: Compound 401-2602-1201 was changed to Compound 402-2602-1201; methacrylic acid was not loaded; and ethylene glycol dimethacrylate (1.113 mmol) was added.

<Synthesis of Polymer 18>

A target polymer 18 was obtained by the same method as that of the synthesis example of the polymer 17 except that Compound 402-2602-1201 was changed to Compound 401-2616-1201.

<Synthesis of Polymer 19>

Compound 502-2621-1201 (0.091 mmol) serving as a polymerizable monomer, neopentyl glycol dimethacrylate (1.113 mmol) serving as a crosslinking agent, azobisisobutyronitrile (0.107 mmol) serving as an initiator, and 3.50 ml of chloroform serving as a solvent were mixed, and then the mixture was heated in a stream of nitrogen at 70° C. for 6 hours to provide a target polymer 19.

<Synthesis of Polymer 20>

A target polymer 20 was obtained by the same method as that of the synthesis example of the polymer 17 except that: Compound 402-2602-1201 was changed to Compound 401-2602-1310; and ethylene glycol dimethacrylate was changed to pentaerythritol tetraacrylate.

<Synthesis of Polymer 21>

A target polymer 21 was obtained by the same method as that of the synthesis example of the polymer 20 except that: Compound 401-2602-1310 was changed to Compound 401-2616-1410; and methacrylic acid (0.122 mmol) was added.

<Synthesis of Polymer 22>

A target polymer 22 was obtained by the same method as that of the synthesis example of the polymer 21 except that Compound 401-2616-1410 was changed to Compound 401-2616-1201.

<Synthesis of Polymer 23>

Compound 502-2621-1201 (0.091 mmol) and styrene (0.122 mmol) serving as polymerizable monomers, divinylbenzene (1.113 mmol) serving as a crosslinking agent, azobisisobutyronitrile (0.107 mmol) serving as an initiator, and 3.50 ml of chloroform serving as a solvent were mixed, and then the mixture was heated in a stream of nitrogen at 70° C. for 6 hours to provide a target polymer 23.

<Synthesis of Polymer 24>

A target polymer 24 was obtained by the same method as that of the synthesis example of the polymer 22 except that: Compound 401-2616-1201 was changed to Compound 401-

2616-1511; and pentaerythritol tetraacrylate was changed to trimethylolpropane trimethacrylate.

<Synthesis of Polymer 25>

Compound 201-2601-601 (0.091 mmol) and vinyl acetate (0.122 mmol) serving as polymerizable monomers, 1-hydroxycyclohexyl phenyl ketone (0.107 mmol) serving as an initiator, and Compound 2407 (0.030 mmol) serving as a template molecule were mixed, and then the mixture was irradiated with UV light (50 mW·cm$^{-2}$, 365 nm, irradiation distance: 123 mm) from a high-pressure mercury lamp "HANDY CURE LAB" (manufactured by SEN LIGHTS Corporation) in a stream of nitrogen for 3 hours to provide a target polymer 25.

<Synthesis of Polymer 26>

A target polymer 26 was obtained by the same method as that of the synthesis example of the polymer 25 except that Compound 201-2601-601 was changed to Compound 201-2608-608.

<Synthesis of Polymer 27>

A target polymer 27 was obtained by the same method as that of the synthesis example of the polymer 25 except that: Compound 201-2601-601 was changed to Compound 202-2616-705; and the template molecule was changed from Compound 2407 to Compound 2411.

<Synthesis of Polymer 28>

A target polymer 28 was obtained by the same method as that of the synthesis example of the polymer 25 except that: Compound 201-2601-601 was changed to Compound 301-2602-601; vinyl acetate was changed to methyl acrylate; and the template molecule was changed from Compound 2407 to Compound 2420.

<Synthesis of Polymer 29>

A target polymer 29 was obtained by the same method as that of the synthesis example of the polymer 28 except that Compound 301-2602-601 was changed to Compound 301-2616-809.

<Synthesis of Polymer 30>

A target polymer 30 was obtained by the same method as that of the synthesis example of the polymer 28 except that: Compound 301-2602-601 was changed to Compound 401-2616-901; and ethylene glycol dimethacrylate (1.113 mmol) was added as a crosslinking agent.

<Synthesis of Polymer 31>

A target polymer 31 was obtained by the same method as that of the synthesis example of the polymer 30 except that: Compound 401-2616-901 was changed to Compound 402-2616-1004; methyl acrylate was not loaded; and the template molecule was changed from Compound 2420 to Compound 2422.

<Synthesis of Polymer 32>

A target polymer 32 was obtained by the same method as that of the synthesis example of the polymer 30 except that: Compound 401-2616-901 was changed to Compound 301-2602-1111; the template molecule was changed from Compound 2420 to Compound 2424; and methyl acrylate was not used.

<Synthesis of Polymer 33>

Compound 301-2602-1111 (0.091 mmol) serving as a polymerizable monomer, 1-hydroxycyclohexyl phenyl ketone (0.107 mmol) serving as an initiator, Compound 2425 (0.030 mmol) serving as a template molecule, and 3.50 ml of chloroform serving as a solvent were mixed, and then the mixture was irradiated with UV light (50 mW·cm$^{-2}$, 365 nm, irradiation distance: 123 mm) from a high-pressure mercury lamp "HANDY CURE LAB" (manufactured by SEN LIGHTS Corporation) in a stream of nitrogen for 3 hours to provide a target polymer 33.

<Synthesis of Polymer 34>

A target polymer 34 was obtained by the same method as that of the synthesis example of the polymer 33 except that: acrylamide (0.122 mmol) serving as a polymerizable monomer was added; and the template molecule was changed from Compound 2425 to Compound 2426.

<Synthesis of Polymer 35>

A target polymer 35 was obtained by the same method as that of the synthesis example of the polymer 34 except that: Compound 301-2602-1111 was changed to Compound 301-2602-1201; and the template molecule was changed from Compound 2426 to Compound 2427.

<Synthesis of Polymer 36>

A target polymer 36 was obtained by the same method as that of the synthesis example of the polymer 35 except that: acrylamide was changed to methacrylamide; and the template molecule was changed from Compound 2427 to Compound 2428.

<Synthesis of Polymer 37>

A target polymer 37 was obtained by the same method as that of the synthesis example of the polymer 35 except that: acrylamide was changed to acrylic acid; and the template molecule was changed from Compound 2427 to Compound 2429.

<Synthesis of Polymer 38>

A target polymer 38 was obtained by the same method as that of the synthesis example of the polymer 35 except that: acrylamide was changed to methacrylic acid; and the template molecule was changed from Compound 2427 to Compound 2430.

<Synthesis of Polymer 39>

A target polymer 39 was obtained by the same method as that of the synthesis example of the polymer 35 except that: acrylamide was changed to N-isopropylacrylamide; and the template molecule was changed from Compound 2427 to Compound 2431.

<Synthesis of Polymer 40>

A target polymer 40 was obtained by the same method as that of the synthesis example of the polymer 38 except that: Compound 301-2602-1201 was changed to Compound 401-2602-1201; and the template molecule was changed from Compound 2430 to Compound 2425.

<Synthesis of Polymer 41>

A target polymer 41 was obtained by the same method as that of the synthesis example of the polymer 40 except that: Compound 401-2602-1201 was changed to Compound 402-2602-1201; methacrylic acid was not added; and ethylene glycol dimethacrylate (1.113 mmol) serving as a crosslinking agent was added.

<Synthesis of Polymer 42>

A target polymer 42 was obtained by the same method as that of the synthesis example of the polymer 41 except that Compound 402-2602-1201 was changed to Compound 401-2616-1201.

<Synthesis of Polymer 43>

Compound 502-2621-1201 (0.091 mmol) serving as a polymerizable monomer, neopentyl glycol dimethacrylate (1.113 mmol) serving as a crosslinking agent, azobisisobutyronitrile (0.107 mmol) serving as an initiator, Compound 2425 (0.030 mmol) serving as a template molecule, and 3.50 ml of chloroform serving as a solvent were mixed, and then the mixture was heated in a stream of nitrogen at 70° C. for 6 hours to provide a target polymer 43.

<Synthesis of Polymer 44>

A target polymer 44 was obtained by the same method as that of the synthesis example of the polymer 41 except that: Compound 402-2602-1201 was changed to Compound 401-

2602-1310; and ethylene glycol dimethacrylate was changed to pentaerythritol tetraacrylate.

<Synthesis of Polymer 45>

A target polymer 45 was obtained by the same method as that of the synthesis example of the polymer 44 except that: Compound 401-2602-1310 was changed to Compound 401-2616-1410; and methacrylic acid (0.122 mmol) was added.

<Synthesis of Polymer 46>

A target polymer 46 was obtained by the same method as that of the synthesis example of the polymer 45 except that: Compound 401-2616-1410 was changed to Compound 401-2616-1201; and the template molecule was changed from Compound 2425 to Compound 2427.

<Synthesis of Polymer 47>

A target polymer 47 was obtained by the same method as that of the synthesis example of the polymer 43 except that: styrene (0.122 mmol) was added as a polymerizable monomer; neopentyl glycol dimethacrylate was changed to divinylbenzene; and the template molecule was changed from Compound 2425 to Compound 2427.

<Synthesis of Polymer 48>

A target polymer 48 was obtained by the same method as that of the synthesis example of the polymer 45 except that: Compound 401-2616-1410 was changed to Compound 401-2616-1511; and pentaerythritol tetraacrylate was changed to trimethylolpropane trimethacrylate.

<Synthesis of Polymer 49>

A target polymer 49 was obtained by the same method as that of the synthesis example of the polymer 47 except that: Compound 502-2621-1201 was changed to Compound 401-2616-1610; styrene was changed to methacrylamide; and the template molecule was changed from Compound 2427 to Compound 2425.

<Synthesis of Polymer 50>

A target polymer 50 was obtained by the same method as that of the synthesis example of the polymer 49 except that: Compound 401-2616-1610 was changed to Compound 401-2616-1712; and the template molecule was changed from Compound 2425 to Compound 2427.

<Synthesis of Polymer 51>

Compound 301-2602-1201 (0.091 mmol) serving as a polymerizable monomer, trimethylolpropane trimethacrylate (1.113 mmol) serving as a crosslinking agent, 1-hydroxycyclohexyl phenyl ketone (0.107 mmol) serving as an initiator, Compound 2416 (0.030 mmol) serving as a template molecule, and 3.50 ml of dimethyl sulfoxide and 0.25 ml of 1-dodecanol serving as solvents were mixed, and then the mixture was irradiated with UV light (50 mW·cm$^{-2}$, 365 nm, irradiation distance: 123 mm) from a high-pressure mercury lamp "HANDY CURE LAB" (manufactured by SEN LIGHTS Corporation) in a stream of nitrogen for 3 hours to provide a target polymer 51.

<Synthesis of Polymer 52>

A target polymer 52 was obtained by the same method as that of the synthesis example of the polymer 51 except that Compound 301-2602-1201 was changed to Compound 402-2602-1201.

<Synthesis of Polymer 53>

A target polymer 53 was obtained by the same method as that of the synthesis example of the polymer 51 except that: Compound 301-2602-1201 was changed to Compound 401-2616-1201; trimethylolpropane trimethacrylate was changed to neopentyl glycol dimethacrylate; and the template molecule was changed from Compound 2416 to Compound 2425.

<Synthesis of Polymer 54>

Compound 401-2616-1201 (0.091 mmol) and N-isopropylacrylamide (0.122 mmol) serving as polymerizable monomers, divinylbenzene (1.113 mmol) serving as a crosslinking agent, azobisisobutyronitrile (0.107 mmol) serving as an initiator, Compound 2427 (0.030 mmol) serving as a template molecule, and 3.50 ml of dimethyl sulfoxide and 0.25 ml of 1-dodecanol serving as solvents were mixed, and then the mixture was heated in a stream of nitrogen at 70° C. for 6 hours to provide a target polymer 54.

<Synthesis of Polymer 55>

A target polymer 55 was obtained by the same method as that of the synthesis example of the polymer 54 except that: N-isopropylacrylamide was changed to methacrylic acid; and the template molecule was changed from Compound 2427 to Compound 2428.

Comparative Examples

<Synthesis of Polymer 56>

Acrylamide (0.091 mmol) serving as a polymerizable monomer, trimethylolpropane trimethacrylate (1.113 mmol) serving as a crosslinking agent, 1-hydroxycyclohexyl phenyl ketone (0.107 mmol) serving as an initiator, Compound 2428 (0.030 mmol) serving as a template molecule, and 3.50 ml of chloroform serving as a solvent were mixed, and then the mixture was irradiated with UV light (50 mW·cm$^{-2}$, 365 nm, irradiation distance: 123 mm) from a high-pressure mercury lamp "HANDY CURE LAB" (manufactured by SEN LIGHTS Corporation) in a stream of nitrogen for 3 hours to provide a target polymer 56.

<Synthesis of Polymer 57>

Styrene (0.091 mmol) serving as a polymerizable monomer, divinylbenzene (1.113 mmol) serving as a crosslinking agent, azobisisobutyronitrile (0.107 mmol) serving as an initiator, Compound 2428 (0.030 mmol) serving as a template molecule, and 3.50 ml of chloroform serving as a solvent were mixed, and then the mixture was heated in a stream of nitrogen at 70° C. for 6 hours to provide a target polymer 57.

<Evaluation>

Methods of calculating sensitivity and specificity in each of Examples of the present invention are listed. Lambda Bio (manufactured by PerkinElmer, Inc.) was used in measurement.

(Calculation of 8-Oxo-2'-deoxyguanosine (8OHdG) Sensitivity)

The absorbance (absr) of 40 µl of an aqueous solution (10 µM) of 8-oxo-2'-deoxyguanosine at 300 nm was measured.

40 Microliters of the aqueous solution (10 µM) of 8-oxo-2'-deoxyguanosine was loaded into 4 mg of each of the polymers 1 to 57, and the mixture was stirred at 20° C. for 24 hours. The mixture was centrifuged at 10,000 rpm, and the absorbance (absk) of a supernatant component thus extracted at 300 nm was measured. A value for the equation "1.0−(absk/absr)" was calculated and defined as the sensitivity of each of the polymer.

In each of Examples of the present invention, the sensitivity was evaluated by the following criteria. Levels A to C were defined as acceptable levels, and a level D was defined as an unacceptable level.

A: Sensitivity of 0.90 or more.
B: Sensitivity of 0.75 or more and less than 0.90.
C: Sensitivity of 0.50 or more and less than 0.75.
D: Sensitivity of less than 0.50.

(Calculation of Specificity)

Uric acid sensitivity was measured by the same method as that in the 8OHdG sensitivity except that 8OHdG was changed to uric acid (manufactured by Kishida Chemical Co., Ltd.). A ratio "8OHdG sensitivity/uric acid sensitivity" was calculated and defined as specificity.

In each of Examples of the present invention, the specificity was evaluated by the following criteria. Levels A to C were defined as acceptable levels, and a level D was defined as an unacceptable level.

A: Specificity of 10.0 or more.
B: Specificity of 5.0 or more and less than 10.0.
C: Specificity of 1.1 or more and less than 5.0.
D: Specificity of less than 1.1.

The sensitivity and specificity of each of the polymers obtained in Examples of the present invention are shown below.

TABLE 1

| Examples | Name | Sensitivity | | Specificity | |
|---|---|---|---|---|---|
| | | Measured value | Evaluation | Measured value | Evaluation |
| Example 1 | Polymer 1 | 0.51 | C | 2.2 | C |
| Example 2 | Polymer 2 | 0.55 | C | 1.8 | C |
| Example 3 | Polymer 3 | 0.53 | C | 1.1 | C |
| Example 4 | Polymer 4 | 0.50 | C | 1.5 | C |
| Example 5 | Polymer 5 | 0.50 | C | 1.1 | C |
| Example 6 | Polymer 6 | 0.59 | C | 1.2 | C |
| Example 7 | Polymer 7 | 0.53 | C | 1.8 | C |
| Example 8 | Polymer 8 | 0.50 | C | 1.2 | C |
| Example 9 | Polymer 9 | 0.52 | C | 1.8 | C |
| Example 10 | Polymer 10 | 0.52 | C | 1.6 | C |
| Example 11 | Polymer 11 | 0.52 | C | 2.1 | C |
| Example 12 | Polymer 12 | 0.53 | C | 2.1 | C |
| Example 13 | Polymer 13 | 0.60 | C | 2.6 | C |
| Example 14 | Polymer 14 | 0.59 | C | 3.3 | C |
| Example 15 | Polymer 15 | 0.53 | C | 2.3 | C |
| Example 16 | Polymer 16 | 0.52 | C | 3.4 | C |
| Example 17 | Polymer 17 | 0.54 | C | 1.9 | C |
| Example 18 | Polymer 18 | 0.54 | C | 2.4 | C |
| Example 19 | Polymer 19 | 0.59 | C | 3.3 | C |
| Example 20 | Polymer 20 | 0.61 | C | 3.0 | C |
| Example 21 | Polymer 21 | 0.66 | C | 3.3 | C |
| Example 22 | Polymer 22 | 0.70 | C | 2.6 | C |
| Example 23 | Polymer 23 | 0.72 | C | 2.8 | C |
| Example 24 | Polymer 24 | 0.68 | C | 3.1 | C |
| Example 25 | Polymer 25 | 0.52 | C | 4.8 | C |
| Example 26 | Polymer 26 | 0.55 | C | 5.6 | B |
| Example 27 | Polymer 27 | 0.65 | C | 6.0 | B |
| Example 28 | Polymer 28 | 0.77 | C | 5.5 | B |
| Example 29 | Polymer 29 | 0.80 | B | 5.5 | B |
| Example 30 | Polymer 30 | 0.75 | B | 4.2 | C |
| Example 31 | Polymer 31 | 0.70 | C | 2.8 | C |
| Example 32 | Polymer 32 | 0.66 | C | 2.2 | C |
| Example 33 | Polymer 33 | 0.78 | B | 4.3 | C |
| Example 34 | Polymer 34 | 0.51 | C | 3.6 | C |
| Example 35 | Polymer 35 | 0.81 | B | 5.1 | B |
| Example 36 | Polymer 36 | 0.76 | B | 5.1 | B |
| Example 37 | Polymer 37 | 0.86 | B | 6.0 | B |
| Example 38 | Polymer 38 | 0.86 | B | 6.6 | B |
| Example 39 | Polymer 39 | 0.77 | B | 5.4 | B |
| Example 40 | Polymer 40 | 0.83 | B | 7.0 | B |
| Example 41 | Polymer 41 | 0.62 | C | 5.2 | B |
| Example 42 | Polymer 42 | 0.64 | C | 5.1 | B |
| Example 43 | Polymer 43 | 0.77 | B | 6.8 | B |
| Example 44 | Polymer 44 | 0.68 | C | 7.1 | B |
| Example 45 | Polymer 45 | 0.74 | C | 10.3 | A |
| Example 46 | Polymer 46 | 0.91 | A | 11.0 | A |
| Example 47 | Polymer 47 | 0.98 | A | 7.9 | B |
| Example 48 | Polymer 48 | 0.95 | A | 12.3 | A |
| Example 49 | Polymer 49 | 0.99 | A | 10.9 | A |
| Example 50 | Polymer 50 | 0.91 | A | 11.9 | A |
| Example 51 | Polymer 51 | 0.81 | B | 13.3 | A |
| Example 52 | Polymer 52 | 0.88 | B | 10.5 | A |
| Example 53 | Polymer 53 | 0.89 | A | 9.7 | B |
| Example 54 | Polymer 54 | 0.92 | A | 12.5 | A |
| Example 55 | Polymer 55 | 0.94 | A | 12.4 | A |

TABLE 1-continued

| Examples | Name | Sensitivity | | Specificity | |
|---|---|---|---|---|---|
| | | Measured value | Evaluation | Measured value | Evaluation |
| Comparative Example 1 | Polymer 56 | 0.44 | D | 1.6 | C |
| Comparative Example 2 | Polymer 57 | 0.70 | C | 0.9 | D |

According to the present invention, there can be provided a polymer represented by the general formula 1, which is capable of adsorbing 8OHdG or a similar marker with high sensitivity and specifically. Thus, there can be provided a method by which 8OHdG is detected simply, with high sensitivity, and specifically.

The polymer of the present invention can perform specific detection of an oxidative stress in a living organism with high sensitivity, at relatively low cost, and simply through the detection of 8-oxo-2'-deoxyguanosine (8OHdG).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-114358, filed Jun. 9, 2017, which is hereby incorporated by reference herein in its entirety.

What is claimed is:

1. A polymer comprising a repetition structure represented by general formula 1:

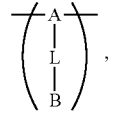

wherein, in the general formula 1:

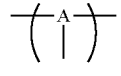

is represented by any one of general formulae 2 to 5;

is represented by any one of general formulae 6 to 11; and
    L represents a divalent linking group containing 1 to 3 carbon atoms for linking A and B:

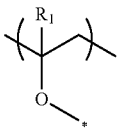

-continued

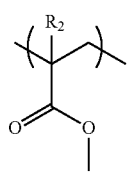

3

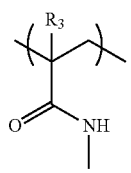

4

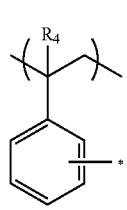

5

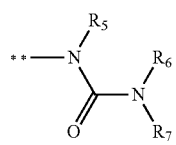

6

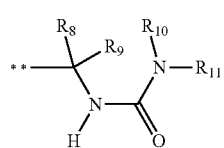

7

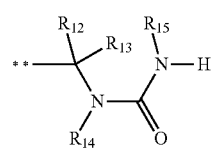

8

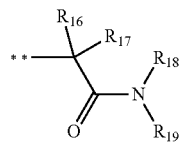

9

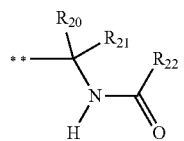

10

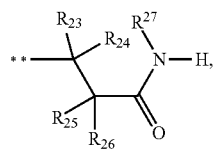

11 wherein, in the general formulae 2 to 5, $R_1$ to $R_4$ each independently represents a hydrogen atom or a methyl group, and * represents a bonding position with L, and wherein, in the general formulae 6 to 11, $R_5$ to $R_{27}$ each independently represents any one of a hydrogen atom, a halogen atom, an alkyl group, an aryl group, a heteroaryl group, an aralkyl group, a hydroxy group, an amino group, a carboxyl group, a sulfo group, and a nitro group, $R_5$ and $R_6$, $R_6$ and $R_7$, $R_8$ and $R_9$, $R_9$ and $R_{10}$, $R_{10}$ and $R_{11}$, $R_{12}$ and $R_{13}$, $R_{13}$ and $R_{15}$, $R_{16}$ and $R_{17}$, $R_{17}$ and $R_{18}$, Rig and $R_{19}$, $R_{20}$ and $R_{21}$, $R_{21}$ and $R_{22}$, $R_{23}$ and $R_{24}$, and $R_{24}$ and $R_{27}$ may each independently be bonded to each other to form a cyclic structure, and ** represents a bonding position with L, and wherein the polymer comprises a repetition structure represented by general formula 26:

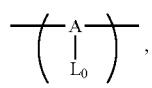

26 wherein, in the general formula 26:

$L_0$ represents a divalent group serving as a crosslinked structure together with $L_0$ of another repetition structure; and

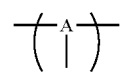

is represented by any one of general formulae 2' to 5':

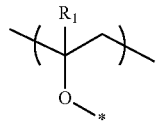

2'

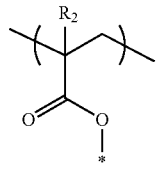

3'

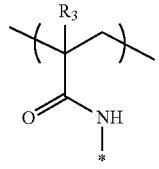

4'

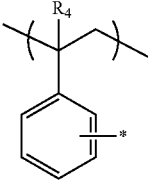

5' wherein, in the formulae 2' to 5', $R_1$ to $R_4$ each independently represents a hydrogen atom or a methyl group, and * represents a bonding position with $L_0$.

2. The polymer according to claim 1, wherein, in the general formula 1,

has a cyclic structure.

3. The polymer according to claim 1, wherein, in the general formula 1,

is represented by any one of general formulae 12 to 17:

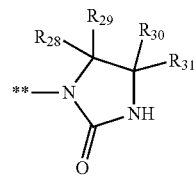   12

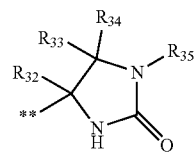   13

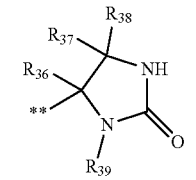   14

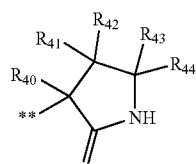   15

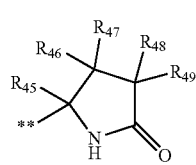   16

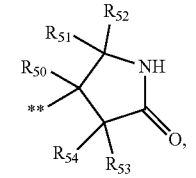   17 wherein, in the general formulae 12 to 17, $R_{28}$ to $R_{54}$ each independently represents any one of a hydrogen atom, a halogen atom, an alkyl group, an aryl group, a heteroaryl group, an aralkyl group, a hydroxy group, an amino group, a carboxyl group, a sulfo group, and a nitro group, and ** represents a bonding position with L.

4. The polymer according to claim 1, wherein the polymer comprises any one of repetition structures represented by general formulae 18 to 23:

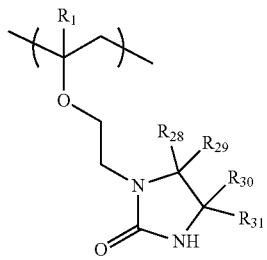   18

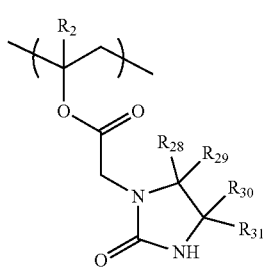   19

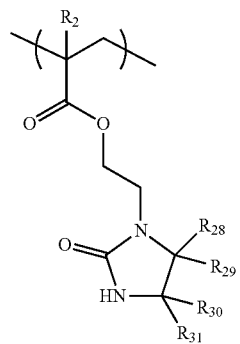   20

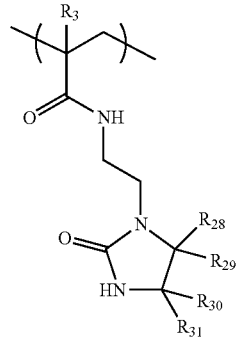   21

-continued

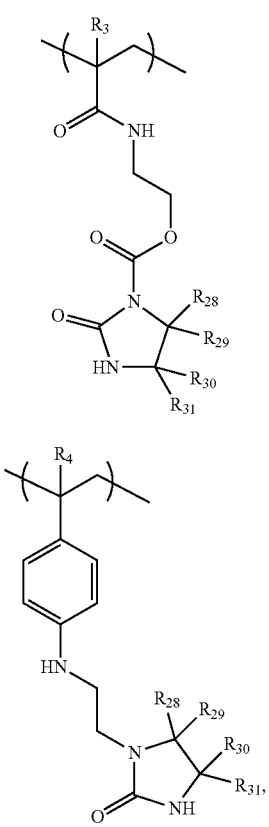

wherein, in the general formulae 18 to 23, $R_1$ to $R_4$ each independently represents a hydrogen atom or a methyl group, and $R_{28}$ to $R_{31}$ each independently represents any one of a hydrogen atom, a halogen atom, an alkyl group, an aryl group, a heteroaryl group, an aralkyl group, a hydroxy group, an amino group, a carboxyl group, a sulfo group, and a nitro group.

5. The polymer according to claim 1, further comprising a repetition structure represented by any one of general formulae 32 to 35:

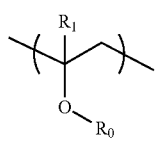

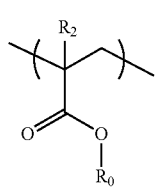

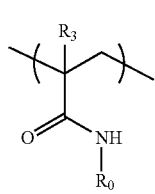

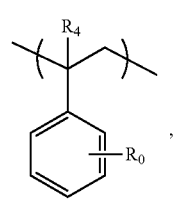

wherein, in the general formulae 32 to 35, $R_0$ represents any one of a hydrogen atom, an alkyl group, an aryl group, a heteroaryl group, an aralkyl group, and an acyl group, and $R_1$ to $R_4$ each independently represents a hydrogen atom or a methyl group.

6. The polymer according to claim 1, wherein the polymer is obtained by performing a polymerization reaction in a presence of a compound represented by general formula 24:

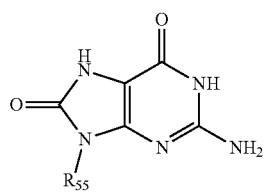

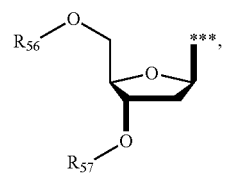

wherein, in the general formula 24, $R_{55}$ represents an alkyl group having 1 to 18 carbon atoms, an aryl group, a heteroaryl group, an aralkyl group, or a structure represented by general formula 25:

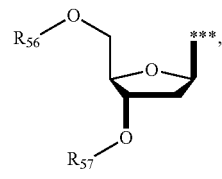

wherein, in the general formula 25, $R_{56}$ and $R_{57}$ each independently represents a hydrogen atom, an alkyl group having 1 to 18 carbon atoms, an aryl group, an acyl group, or a silyl group, and *** represents a bonding position with a nitrogen atom in the general formula 24.

* * * * *